United States Patent [19]

Tominaga et al.

[11] Patent Number: 4,468,402
[45] Date of Patent: Aug. 28, 1984

[54] CARBOSTYRIL DERIVATIVES, PROCESS FOR PRODUCING THE SAME AND CARDIOTONIC COMPOSITIONS CONTAINING THE SAME

[75] Inventors: Michiaki Tominaga; Yung-hsiung Yang; Hidenori Ogawa; Kazuyuki Nakagawa, all of Tokushima, Japan

[73] Assignee: Otsuka Pharmaceutical Co., Ltd., Japan

[21] Appl. No.: 525,284

[22] Filed: Aug. 22, 1983

Related U.S. Application Data

[62] Division of Ser. No. 348,709, Feb. 16, 1982.

[30] Foreign Application Priority Data

Feb. 17, 1981 [JP] Japan ..................... 56-22437
Apr. 15, 1981 [JP] Japan ..................... 56-57732
Aug. 12, 1981 [JP] Japan ..................... 56-127145

[51] Int. Cl.$^3$ ................ C07D 215/20; A61K 31/47
[52] U.S. Cl. ..................... 424/258; 546/157; 546/158; 544/128; 544/363; 424/248.4; 424/250
[58] Field of Search ................ 546/157, 158; 424/258

[56] References Cited

U.S. PATENT DOCUMENTS

| | | | |
|---|---|---|---|
| 3,555,030 | 1/1971 | Loev et al. ................ | 546/158 |
| 3,994,900 | 11/1976 | Krapcho et al. ............ | 546/158 |
| 4,022,776 | 5/1977 | Nakagawa et al. .......... | 544/128 |
| 4,022,784 | 5/1977 | Nakagawa et al. .......... | 544/128 |
| 4,070,470 | 1/1978 | Nakagawa et al. .......... | 546/158 |
| 4,210,753 | 7/1980 | Tominaga et al. .......... | 544/128 |
| 4,223,137 | 9/1980 | Yoshizaki et al. .......... | 544/128 |
| 4,256,890 | 3/1981 | Nakagawa et al. .......... | 544/128 |
| 4,298,739 | 11/1981 | Nishi et al. ............... | 546/158 |

FOREIGN PATENT DOCUMENTS 2094789 9/1982 United Kingdom ................ 546/158

*Primary Examiner*—Donald G. Daus
*Assistant Examiner*—S. A. Gibson
*Attorney, Agent, or Firm*—Finnegan, Henderson, Farabow, Garrett & Dunner

[57] ABSTRACT

Novel carbostyril derivatives and their pharmaceutically acceptable salts represented by the formula (I)

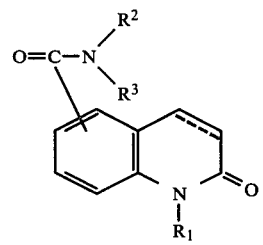

wherein $R^1$ is a hydrogen atom, a lower alkyl group, a lower alkenyl group, a lower alkynyl group or a phenyl-lower alkyl group; $R^2$ and $R^3$ may be the same or different and each is a lower alkyl group which may have one hydroxy group or one halogen atom as the substituent, or a phenyl-lower alkyl group which may have 1 to 3 substituents selected from the group consisting of a lower alkoxy group and a halogen atom on the phenyl ring, or said phenyl-lower allkyl group may have a lower alkylenedioxy group as the substituent on the phenyl ring; further $R^2$ and $R^3$ may form, together with the adjacent nitrogen and without an additional hetero-atom, a 5-or 6 membered saturated heterocyclic ring which may have a lower alkyl group or a phenyl-lower alkyl group as the substituent; the carbon-carbon bond between 3- and 4-positions in the carbostyril skeleton being a single or double bond. The derivatives are useful as the active ingredient in cardiotonic compositions.

2 Claims, No Drawings

CARBOSTYRIL DERIVATIVES, PROCESS FOR PRODUCING THE SAME AND CARDIOTONIC COMPOSITIONS CONTAINING THE SAME

This is a division of application Ser. No. 06/348,709, filed Feb. 16, 1982.

The present invention relates to novel carbostyril derivatives and their salts, processes for producing the same and cardiotonic compositions containing the same as the active ingredients.

Carbostyril derivatives and their salts of the present invention are represented by the following general formula (1).

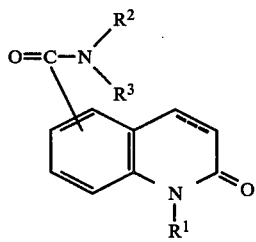

wherein $R^1$ is a hydrogen atom, a lower alkyl group, a lower alkenyl group, a lower alkynyl group or a phenyl-lower alkyl group; $R^2$ and $R^3$ may be the same or different and each are a lower alkyl group which may have hydroxy group(s) or halogen atom(s) as the substituent(s), or a phenyl-lower alkyl group which may have 1 to 3 substituents selected from the group consisting of a lower alkoxy group and a halogen atom on the phenyl ring, or said phenyl-lower alkyl group may have a lower alkylenedioxy group as the substituent on the phenyl ring; further $R^2$ and $R^3$ may form, together with the adjacent nitrogen atom and further with or without an additional oxygen or nitrogen atom, a 5- or 6-membered saturated heterocyclic ring which may have a lower alkyl group or a phenyl-lower alkyl group as the substituent; when said heterocyclic ring is a piperazinyl group, the piperazinyl ring may have a lower alkyl group or a phenyl-lower alkyl group as the substituent at 4-position in the piperazinyl ring, further said piperazinyl group may have, as the substituent at 4-position, a lower alkenyl group, a lower alkynyl group, a cycloalkyl group, a cycloalkyl-lower alkyl group, a lower alkanoyl group, a lower alkanoyl-lower alkyl group, a lower alkoxycarbonyl group, a lower alkoxycarbonyl-lower alkyl group, a furoyl group, a lower alkylsulfonyl group, a substituted lower alkyl group (having one substituent selected from the group consisting of a cyano group, a benzoyloxy group (which may have 1 to 3 lower alkoxy groups on the phenyl ring), a hydroxy group, a lower alkanoyloxy group, a halogen atom and a carbamoyl group), a phenoxy-lower alkyl group (which may have, on the phenyl ring, 1 to 3 substituents selected from the group consisting of a halogen atom, a lower alkoxy group and a lower alkyl group, or said phenoxy-lower alkyl group may have, on the phenyl ring, a lower alkylenedioxy group as the substituent), a phenyl-lower alkyl group (which may have, on the phenyl ring, 1 to 3 substituents selected from the group consisting of lower alkyl group, a lower alkoxy group, a halogen atom, a nitro group, an amino group, a lower alkanoylamino group and a lower alkylthio group, or said phenyl-lower alkyl group may have, on the phenyl ring, a lower alkylenedioxy group as the substituent), a benzoyl group (which may have, on the phenyl ring, 1 to 3 substituents selected from the group consisting of a lower alkyl group, a lower alkoxy group, a halogen atom, a nitro group and a cyano group, or said benzoyl group may have, on the phenyl ring, a lower alkylenedioxy group as the substituent), a phenylsulfonyl group (which may have, on the phenyl ring, 1 to 3 lower alkyl groups as the substituents), a benzoyl-lower alkyl group (which may have, on the phenyl ring, 1 to 3 substituents selected from the group consisting of a halogen atom, a hydroxy group, a lower alkyl group, a lower alkoxy group and a lower alkanoylamino group), a phenyl-lower alkenylcarbonyl group (which may have, on the phenyl ring, 1 to 3 substituents selected from the group consisting of a halogen atom, and a lower alkoxy group), or a phenyl-lower alkanoyl group (which may have, on the pheny ring, 1 to 3 lower alkoxy groups as the substituents); the carbon-carbon bond between 3- and 4-positions in the carbostyril skeleton is a single or double bond.

Carbostyril derivatives of the present invention represented by the general formula (1) have myocardial contraction increasing activity (positive inotropic activity), coronary blood flow increasing activity and hypotensive activity, and thus they are useful as cardiotonics for curing various heat diseases such as congestive heart failure, mitral valvular disease, atrial fibrillation and flutter and paroxysmal artrial tachycardia.

Specifically, carbostyril derivatives of the present invention represented by the general formula (1) have excellent properties in positive inotropic activity, coronary blood flow increasing activity and hypotensive activity, while they have almost no heart beat increasing activity.

Some carbostyril derivatives having useful pharmacological activities, such as bronchiectactic agent, anti-histaminic agent, anti-hypertensive agent and central nervous system controlling agent are known in prior art literatures, for example:

(a) Japanese Patent Application Kokai (Laid-open) No. 12515/1978 discloses carbostyril derivatives having side-chain of the formula,

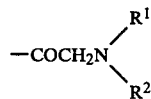

(wherein $R^1$ and $R^2$ may form, together with the adjacent nitrogen atom, a substituted or unsubstituted heterocyclic ring), on the contrary the carbostyril derivatives represented by the general formula (1) of the present invention having the side chain of the formula

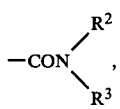

thus the carbonyl group —CO— is connected to the group of the formula

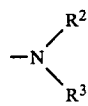

directly, without connected through a methylene group of the formula —CH$_2$—. The carbostyril derivatives disclosed in this literature (a) are useful as intermediate compounds for preparing pharmaceutical chemicals such as telangietatic agents, hypotensive agents and the like. In this connection, the inventors believe that the pharmacological activities of compounds having side-chain of which chemical structural formulas are different from those of the carbostyril derivatives represented by the general formula (1) of the present invention should be different from the latter.

(b) Japanese Patent Application Kokai (Laid-open) No. 118771/1976 discloses carbostyril derivatives having side-chain of the formula

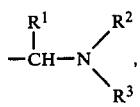

thus similar to the side-chain as explained in the literature (a) above, the carbonyl group —CO— is connected to the group of the formula

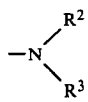

through group of the formula

Also the pharmacological activities of carbostyril derivatives disclosed in this literature (b) are different from those of carbostyril derivative represented by the general formula (1) of the present invention. The carbostyril derivatives of this literature (b) are useful as intermediate compounds for preparing pharmaceutical chemicals such as telangietatic agent an the like.

(c) Japanese Patent Application Kokai (Laid-open) No. 16478/1979 discloses carbostyril derivatives having side-chain wherein the carbonyl group —CO— and the group of the formula

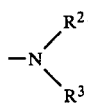

are connected through a group of the formula

and the pharmacological activities thereof are also different from those of carbostyril derivatives represented by the general formula (1) of the present invention. Carbostyril derivative disclosed in this literature (c) are useful as bronchietatic agent, antihistaminic agent and anti-hypertensive agent.

(d) Belgian Pat. No. 887800 and (e) British patent application (Laid-open) No. 2071-094 disclose carbostyril derivatives having side-chain wherein the carbonyl group —CO— and a group of the formula

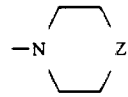

are connected to each other through a lower alkyl group. The pharmacological activities of carbostyril derivatives disclosed in these literatures are different from those of the carbostyril derivatives represented by the general formula (1) of the present invention. The carbostyril derivatives disclosed in these literatures are useful as central nervous system controlling agent and antihistaminic agent.

(f) Japanese Patent Application Kokai (Laid-open) No. 16470/1981 discloses carbostyril derivatives having side-chain of the formula —O—D—SO$_m$—R$^2$ which is essentially different from the side-chain of the formula

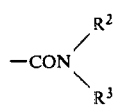

being contained in the carbostyril derivatives represented by the general formula (1) of the present invention.

The carbostyril derivatives disclosed in this literature (f) indeed have positive inotropic activity (myocardial contraction increasing activity) and anti-thrombotic activity, thus one of the pharmacological activities thereof (myocardial increasing activity) is similar to the pharmacological activity being shown by carbostyril derivatives represented by the general formula (1) of the present invention, but type of the side chain contained in the former carbostyril derivatives is different from that contained in the latter carbostyril derivatives.

Next, concrete examples of the groups as defined in the symbols R$^1$, R$^2$ and R$^3$ in the general formula (1) are exemplified as follows:

The expression "a lower alkyl group" means a straight chain or branched chain alkyl group having 1 to 6 carbon atoms and the examples including methyl, ethyl, propyl, isopropyl, butyl, tert-butyl, pentyl and hexyl groups and the like.

The expression "a lower alkenyl group" means a straight chain or branched chain alkenyl group having 2 to 6 carbon atoms, and the examples including vinyl, allyl, 2-butenyl, 3-butenyl, 1-methylallyl, 2-pentenyl and 2-hexenyl groups and the like.

The expression "a lower alkynyl group" means a straight chain or branched chain alkynyl group having 2 to 6 carbon atoms, and the examples including ethynyl, 2-propynyl, 2-butynyl, 1-methyl-2-propynyl, 2-pentynyl and 2-hexynyl groups and the like.

The expression "a phenyl-lower alkyl group" means a phenylalkyl group in which the alkyl group is a straight chain or branched chain alkyl group having 1 to 6 carbon atoms, and the examples including benzyl, 2- phenylethyl, 1-phenylethyl, 3-phenylpropyl, 4-phenylbutyl, 1,1-dimethyl-2-phenylethyl, 5-phenylpentyl, 6-phenylhexyl and 2-methyl-3-phenylpropyl groups and the like.

The expression "cycloalkyl-lower alkyl group" means a straight chain or branched chain alkyl group having 1 to 6 carbon atoms to which a cycloalkyl group having 3 to 8 carbon atoms is attached, and the examples including cyclopropylmethyl, 4-cyclohexylbutyl, 2-cyclopentylethyl, cyclohexylmethyl, 2-cyclopentylpropyl, 3-cyclohexylpropyl, cyclopentylmethyl, 2-cyclohexylethyl, 2-cyclohexylpropyl, 2-cycloheptylethyl, 3-cyclobutylpropyl, 1,1-dimethyl-2-cyclohexylethyl, 1-methyl-2-cyclopentylethyl, 2-cyclooctylethyl, 5-cyclohexylpentyl, and 6-cyclohexylhexyl groups and the like.

The expression "a lower alkanoyl group" means a straight chain or branched chain alkanoyl group having 1 to 6 carbon atoms in the alkyl moiety, and the examples including formyl, acetyl, propionyl, butyryl, isobutyryl, pentanoyl, tertbutylcarbonyl and hexanoyl groups and the like.

The expression "a lower alkoxycarbonyl group" means a straight chain or branched chain alkoxycarbonyl group in which the alkoxy group having 1 to 6 carbon atoms, and the examples including methoxycarbonyl, ethoxycarbonyl, propoxycarbonyl, isopropoxycarbonyl, butoxycarbonyl, tert-butoxycarbonyl, pentyloxycarbonyl and hexyloxycarbonyl groups and the like.

The expression "a lower alkylsulfonyl group" means a straight chain or branched chain alkylsulfonyl group having 1 to 6 carbon atoms, and the examples including methanesulfonyl, ethanesulfonyl, propanesulfonyl, isopropanesulfonyl, butanesulfonyl, tert-butanesulfonyl and pentanesulfonyl and hexanesulfonyl groups and the like.

The expression "a phenoxy-lower alkyl group (which may have, on the phenyl ring, 1 to 3 substituents selected from the group consisting of a halogen atom, a lower alkoxy group and a lower alkyl group, or said phenoxy-lower alkyl group may have, on the phenyl ring, a lower alkylenedioxy group as the substituent)" means a straight chain or branched chain alkyl group having 1 to 6 carbon atoms to which a phenoxy group is attached, said phenoxy group may have, on the phenyl ring, 1 to 3 substituents selected from the group consisting of a halogen atom, an alkoxy group having 1 to 6 carbon atoms and an alkyl group having 1 to 6 carbon atoms, or said phenoxy group may have, on the phenyl ring, an alkylenedioxy group having 1 to 4 carbon atoms as the substituent, and the examples including phenoxymethyl, 2-phenoxyethyl, 2-phenoxypropyl, 3-phenoxypropyl, 1-methyl-2-phenoxyethyl, 2-phenoxybutyl, 3-phenoxybutyl, 4-phenoxybutyl, 1,1-dimethyl-2-phenoxybutyl, 2-phenoxypentyl, 3-phenoxypentyl, 4-phenoxyhexyl, (2-methoxyphenoxy)methyl, (3-methoxyphenoxy)methyl, 2-(4-methoxyphenoxy)ethyl, (2-ethoxyphenoxy)methyl, 1-(3-ethoxyphenoxy)ethyl, 3-(4-ethoxyphenoxy)propyl, 6-(4-isopropoxyphenoxy)hexyl, 4-(4-hexyloxyphenoxy)butyl, 1,1-dimethyl-2-(3,4-dimethoxyphenoxy)ethyl, 5-(3,4-diethoxyphenoxy)pentyl, 6-(3,4,5-trimethoxyphenoxy)hexyl, 2-methyl-3-(2,5-dimethoxyphenoxy)propyl, (2-chlorophenoxy)methyl, (3-bromophenoxy)methyl, (4-iodophenoxy)methyl, 2-(4-fluorophenoxy)ethyl, 1-(3-chlorophenoxy)ethyl, 6-(4-bromophenoxy)hexyl, 5-(3,4-dichlorophenoxy)pentyl, 1,1-dimethyl-2-(2,5-dibromophenoxy)propyl, (3,4,5-trichlorophenoxy)methyl, (2-ethylphenoxy)methyl, (3-methylphenoxy)methyl, 2-(4-methylphenoxy)ethyl, (2-ethylphenoxy)methyl, 1-(3-ethylphenoxy)ethyl, 3-(4-ethylphenoxy)propyl, 6-(4-isopropylphenoxy)hexyl, 4-(4-hexylphenoxy)butyl, 1,1-dimethyl-2-(3,4-dimethylphenoxy)ethyl, 5-(3,4-diethylphenoxy)pentyl, 6-(3,5-dimethylphenoxy)hexyl, 2-methyl-3-(2,5-dimethylphenoxy)propyl, (3,4-methylenedioxyphenoxy)methyl, 2-(3,4-methylenedioxyphenoxy)ethyl, 2-(3,4-ethylenedioxyphenoxy)ethyl, 2-(2,3-methylenedioxyphenoxy)ethyl, 2-(3,4-trimethylenedioxyphenoxy)ethyl, 4-(3,4-methylenedioxyphenoxy)butyl, (3,4-ethylenedioxyphenoxy)methyl, (2,3-methylenedioxyphenoxy)methyl, 1-(3,4-methylenedioxyphenoxy)ethyl, 3-(3,4-methylenedioxyphenoxy)propyl, 6-(3,4-methylenedioxyphenoxy)hexyl, (3,4,5-trimethylphenoxy)methyl, (3,4,5-trimethoxyphenoxy)methyl and 2-(3,4,5-trimethoxyphenoxy)ethyl groups and the like.

The expression "a substituted lower alkyl group (having one substituent selected from the group consisting of a cyano group, a benzoyloxy group (which may have 1 to 3 lower alkoxy groups, as the substituents, on the phenyl ring), a hydroxy group, a lower alkanoyloxy group, a halogen atom and a carbamoyl group)" means a straight chain or branched chain alkyl group having 1 to 6 carbon atoms, containing one substituent selected from the group consisting of a cyano group, a benzoyloxy group (which may have 1 to 3 straight chain or branched chain alkoxy groups on the phenyl ring), a hydroxy group, a straight chain or branched chain alkanoyloxy group having 1 to 6 carbon atoms in the alkyl moiety, a halogen atom and a carbamoyl group, and the examples including cyanomethyl, carbamoylmethyl, 2-cyanoethyl, 2-carbamoylethyl, 2-cyanopropyl, 3-cyanopropyl, 2-carbamoylpropyl, 3-carbamoylpropyl, 1-methyl-2-cyanoethyl, 1-methyl-2-carbamoylethyl, 2-cyanobutyl, 3-cyanobutyl, 4-cyanobutyl, 2-carbamoylbutyl, 3-carbamoylbutyl, 4-carbamoylbutyl, 1,1-dimethyl-2-cyanobutyl, 1,1-dimethyl-2-carbamoylbutyl, 2-cyanopentyl, 3-cyanopentyl, 2-carbamoylpentyl, 3-carbamoylpentyl, 4-cyanohexyl, 4-carbamoylhexyl, hydroxymethyl, 2-hydroxyethyl, 2-hydroxypropyl, 2-hydroxybutyl, 3-hydroxypropyl, 4-hydroxybutyl, 3-hydroxybutyl, 5-hydroxypentyl, 6-hydroxyhexyl, acetyloxymethyl, 2-acetyloxyethyl, 2-acetyloxypropyl, 3-acetyloxypropyl, 4-acetyloxybutyl, 3-acetyloxybutyl, 5-acetyloxypentyl, 6-acetyloxyhexyl, 2-propionyloxyethyl, 3-formyloxypropyl, 2-butyryloxypropyl, 4-isobutyryloxybutyl, 2-pentanoyloxyethyl, tert-butylcarbonyloxymethyl, 2-hexanoyloxyethyl, benzoyloxymethyl, 2-benzoyloxyethyl, 3-benzoyloxypropyl, 6-benzoyloxyhexyl, 4-benzoyloxybutyl, 2-methoxybenzoyloxymethyl, 3-methoxybenzoyloxymethyl, 2-(4-methoxybenzoyloxy)ethyl, 2-ethoxybenzoyloxymethyl, 1-(3-ethoxybenzoyloxy)ethyl, 3-(4-ethoxybenzoyloxy)propyl, 6-(4-isopropoxybenzoyloxy)hexyl, 4-(4-hexyloxybenzoyloxy)butyl, 1,1-dimethyl-2-(3,4-dimethylbenzoyloxy)ethyl, 5-benzoyloxypentyl, 5-(3,4-diethoxybenzoyloxy)pentyl, 6-(3,4,5-trimethoxybenzoyloxy)hexyl, 2-methyl-3-(2,5-dimethoxybenzoyloxy)propyl, 2-(3,4-dimethoxybenzoyloxy)ethyl, 3-(3,4,5-trimethoxybenzoyloxy)propyl, chloromethyl, bromomethyl, iodomethyl, fluoromethyl, 2-chloroethyl, 2-bromoethyl, 2-chloropropyl, 3-chloropropyl, 2-fluoropropyl, 3-iodopropyl, 1-methyl-2-chloroethyl, 2-bromobutyl, 3-bromobutyl, 4-bromobutyl, 3-chlorobutyl, 2-iodobutyl, 4-fluorobutyl, 1,1-dimethyl-2- chlorobutyl, 2-chloropentyl, 3-chloropentyl, 4-bromohexyl, 6-chlorohexyl and 5-bromopentyl groups and the like.

The expression "a phenyl-lower alkyl group (which may have, on the phenyl ring, 1 to 3 substituents selected from the group consisting of a lower alkyl group, a lower alkoxy group, a halogen atom, a nitro group, an amino group, a lower alkanoylamino group and a lower alkylthio group, or said phenyl-lower alkyl group may have, on the phenyl ring, a lower alkylenedioxy group as the substituent)" means a straight chain or branched chain alkyl group having 1 to 6 carbon atoms, to which one or two phenyl groups are attached, said phenyl groups may respectively have, 1 to 3 substituents selected from the group consisting of a straight chain or branched chain alkyl group having 1 to 6 carbon atoms, a straight chain or branched chain alkoxy group having 1 to 6 carbon atoms, a halogen atom, a nitro group, an amino group, a straight chain or branched chain alkanoylamino group having 1 to 6 carbon atoms in the alkyl moiety, and a straight chain or branched chain alkylthio group having 1 to 6 carbon atoms, or said phenyl-alkyl group may have, on the phenyl ring, an alkylenedioxy group having 1 to 4 carbon atoms as the substituent, and the examples including benzyl, 2-phenylethyl, 3-phenylpropyl, 6-phenylhexyl, 4-phenylbutyl, diphenylmethyl, 1,2-diphenylethyl, 2-methoxybenzyl, 3-methoxybenzyl, 2-(4-methoxyphenyl)ethyl, 2-ethoxybenzyl, 1-(3-ethoxyphenyl)ethyl, 3-(4-ethoxyphenyl)propyl, 6-(4-isopropoxyphenyl)hexyl, 4-(4-hexyloxyphenyl)butyl, 1,1-dimethyl-2-(3,4-dimethoxyphenyl)ethyl, 5-phenylpentyl, 5-(3,4-diethoxyphenyl)pentyl, 6-(3,4,5-trimethoxyphenyl)hexyl, 2-methyl-3-(2,5-dimethoxyphenyl)propyl, 2-nitrobenzyl, 3-nitrobenzyl, 1-(3-nitrophenyl)ethyl, 6-(4-nitrophenyl)hexyl, 2-chlorobenzyl, 3-bromobenzyl, 4-iodobenzyl, 2-(4-fluorophenyl)ethyl, 1-(3-chlorophenyl)ethyl, 6-(4-bromophenyl)hexyl, 5-(3,4-dichlorophenyl)pentyl, 1,1-dimethyl-2-(2,5-dibromophenyl)propyl, 2-methylbenzyl, 3-methylbenzyl, 2-(4-methylphenyl)ethyl, 2-ethylbenzyl, 1-(3-ethylphenyl)ethyl, 3-(4-ethylphenyl)propyl, 6-(4-isopropylphenyl)hexyl, 4-(4-hexylphenyl)butyl, 1,1-dimethyl-2-(3,4-dimethylphenyl)ethyl, 5-(3,4-diethylphenyl)pentyl, 6-(3,5-dimethylphenyl)hexyl, 2-methyl-3-(2,5-dimethylphenyl)propyl, 2-aminobenzyl, 3-aminobenzyl, 1-(3-aminophenyl)ethyl, 6-(4-aminophenyl)hexyl, 2-acetylaminobenzyl, 3-formylaminobenzyl, 1-(3-propionylaminophenyl)ethyl, 6-(4-n-butyrylaminophenyl)hexyl, 2-(5-pentanoylaminophenyl)ethyl, 4-(6-hexamoylaminophenyl)butyl, 2-methylthiobenzyl, 3-methylthiobenzyl, 2-(4-methylthiophenyl)ethyl, 2-ethylthiobenzyl, 1-(3-ethylthiophenyl)ethyl, 3-(4-ethylthiophenyl)propyl, 6-(4-isopropylthiophenyl)hexyl, 4-(4-hexylthiophenyl)butyl, 1,1-dimethyl-2-(3,4-dimethylthiophenyl)ethyl, 5-(3,4-diethylthiophenyl)pentyl, 6-(3,5-dimethylthiophenyl)hexyl, 2-methyl-3-(2,5-dimethylthiophenyl)propyl, 3-methyl-4-chlorobenzyl, 2-chloro-6-methylbenzyl, 2-methoxy-3-chlorobenzyl, phenyl(4-chlorophenyl)methyl, di(4-methylphenyl)methyl, phenyl(3-methoxyphenyl)methyl, 3,4,5-trimethoxybenzyl, 2-(3,4,5-trimethoxyphenyl)ethyl, 3,4,5-trimethylbenzyl, 3,4-ethylenedioxybenzyl, 2,3-methylenedioxybenzyl, 1-(3,4-methylenedioxyphenyl)ethyl, 3-(3,4-methylenedioxyphenyl)propyl, 6-(3,4-methylenedioxyphenyl)hexyl, 3,4,5-trichlorobenzyl, 3,4-methylenedioxybenzyl, 2-(3,4-methylenedioxyphenyl)ethyl, 2-(3,4-ethylenedioxyphenyl)ethyl, 2-(2,3-methylendioxyphenyl)ethyl, 2-(3,4-trimethylenedioxyphenyl)ethyl and 4-(3,4-methylenedioxyphenyl)butyl groups and the like.

The expression "a benzoyl group (which may have, on the phenyl ring, 1 to 3 substituents selected from the group consisting of a lower alkyl group, a lower alkoxy group, a halogen atom, a nitro group and a cyano group, or said benzoyl group may have, on the phenyl ring, a lower alkylenedioxy group as the substituent)" means a benzoyl group which may have, on the phenyl ring, 1 to 3 substituents selected from the group consisting of a straight chain or branched chain alkyl group having 1 to 6 carbon atoms, a straight chain or branched chain alkoxy group having 1 to 6 carbon atoms, a halogen atom, a nitro group and a cyano group, or said benzoyl group may have, on the phenyl ring, an alkylenedioxy group having 1 to 4 carbon atoms, and the examples including 2-chlorobenzoyl, 3-chlorobenzoyl, 4-chlorobenzoyl, 2-fluorobenzoyl, 3-fluorobenzoyl, 4-fluorobenzoyl, 2-bromobenzoyl, 3-bromobenzoyl, 4-bromobenzoyl, 2-iodobenzoyl, 3-iodobenzoyl, 4-iodobenzoyl, 3,5-dichlorobenzoyl, 2,6-dichlorobenzoyl, 3,4-dichlorobenzoyl, 3,4-difluorobenzoyl, 3,5-dibromobenzoyl, 2-methylbenzoyl, 3-methylbenzoyl, 4-methylbenzoyl, 2-ethylbenzoyl, 3-ethylbenzoyl, 4-ethylbenzoyl, 3-isopropylbenzoyl, 4-hexylbenzoyl, 3,4-dimethylbenzoyl, 2,5-dimethylbenzoyl, 2-methoxybenzoyl, 3-methoxybenzoyl 4-methoxybenzoyl, 2-ethoxybenzoyl, 3-ethoxybenzoyl, 4-ethoxybenzoyl, 4-isopropoxybenzoyl, 4-hexyloxybenzoyl, 3,4-dimethoxybenzoyl, 3,4-diethoxybenzoyl, 2,5-dimethoxybenzoyl, 2-nitrobenzoyl, 3-nitrobenzoyl, 4-nitrobenzoyl, 2,4-dinitrobenzoyl, 2-cyanobenzoyl, 3-cyanobenzoyl, 4-cyanobenzoyl, 2,4-dicyanobenzoyl, 3,4-methylenedioxybenzoyl, 3,4-ethylenedioxybenzoyl, 2,3-methylenedioxybenzoyl, 3,4-trimethylenedioxybenzoyl, 2,3-tetramethylenedioxybenzoyl, 3-methyl-4-chlorobenzoyl, 2-chloro-6-methylbenzoyl, 2-methoxy-3-chlorobenzoyl, 3,4,5-trimethoxybenzoyl, 3,4,5-trimethylbenzoyl and 3,4,5-trichlorobenzoyl groups and the like.

The expression "a phenyl-sulfonyl group (which may have, on the phenyl ring, 1 to 3 lower alkyl groups as the substituents)" means a phenylsulfonyl group which may have, on the phenyl ring, 1 to 3 alkyl group having 1 to 6 carbon atoms as the substituents, and the examples including phenylsulfonyl, toluenesulfonyl, xylenesulfonyl, trimethylbenzenesulfonyl, ethylbenzenesulfonyl, isopropylbenzenesulfonyl, butylbenzenesulfonyl and hexylbenzenesulfonyl groups and the like.

The expression "a phenyl-lower alkyl group which may have 1 to 3 substituents selected from the group consisting of a lower alkoxy group and a halogen atom on the phenyl ring, or said phenyl-lower alkyl group may have a lower alkylenedioxy group as the substituent on the phenyl ring" means a straight chain or branched chain alkyl group having 1 to 6 carbon atoms, to which one or two phenyl groups are attached, said phenyl group may have 1 to 3 substituents selected from the group consisting of a straight chain or branched chain alkoxy group having 1 to 6 carbon atoms and a halogen atom, or said phenyl group may have a straight chain or branched chain alkylenedioxy group having 1 to 4 carbon atoms as the substituents, and the examples including benzyl, 2-phenylethyl, 1-phenylethyl, 3-phenylpropyl, 4-phenylbutyl, 1,1-dimethyl-2-phenylethyl, 5phenylpentyl, 6-phenylhexy, 2-methyl-3-phenylpropyl, diphenylmethyl, 2,2-diphenylethyl, 3,3-diphenylpropyl, 1,1-dimethyl-2,2-diphenylethyl, 2-methoxybenzyl, 3-methoxybenzyl, 4-methoxybenzyl, 3-ethoxybenzyl, 2-propoxybenzyl, 3-isopropoxybenzyl, 4-tert-butoxybenzyl, 2-(4-methoxyphenyl)ethyl, 2-(4-methoxyphenyl)ethyl, 2-(2-ethoxyphenyl)ethyl, 2-(3-butoxyphenyl)ethyl, 1-(4-ethoxyphenyl)ethyl, 3-(2-methoxypheny)propyl, 2-methyl-3-(4-methoxyphenyl)propyl, 6-(4-methoxyphenyl)hexyl, 2-chlorobenzyl, 3-chlorobenzyl, 4-bromobenzyl, 2-iodobenzyl, 3-fluorobenzyl, 2-(3-chlorophenyl)ethyl, 2-(4-chlorophenyl)ethyl, 2-(2-bromophenyl)ethyl, 2-(3-iodophenyl)ethyl, 1-(4-chlorophenyl)ethyl, 1-(3-bromophenyl)ethyl, 3-(2-chlorophenyl)propyl, 3-(4-chlorophenyl)propyl, 3-(3-bromophenyl)propyl, 3-(4-iodophenyl) propyl, 5-(3-chlorophenyl)pentyl, 2,3-methylenedioxybenzyl, 3,4-methylenedioxybenzyl, 2,3-ethylenedioxybenzyl, 3,4-ethylenedioxybenzyl, 3,4-trimethylenedioxybenzyl, 2-(2,3-methylenedioxyphenyl)ethyl, 2-(3,4-ethylenedioxyphenyl)ethyl, 1-(3,4-methylenedioxyphenyl)ethyl, 3-(2,3-methylenedioxyphenyl)propyl, 3-(3,4-ethylenedioxyphenyl)propyl, 1,1-dimethyl-2-(3,4-methylenedioxyphenyl)ethyl, 2-methyl-3-(3,4-ethylenedioxyphenyl)propyl, 2,3-dimethoxybenzyl, 2,4-dimethoxybenzyl, 3,4,5-trimethoxybenzyl, 2,4-diethoxybenzyl, 2-(3,4-diethoxyphenyl)ethyl, 2-(3,4,5-trimethoxyphenyl)ethyl, 3-(2,3-dimethoxyphenyl)propyl, 3-(3-methoxy-4-ethoxyphenyl)propyl, 1,1-dimethyl-2-(3,4,5-trimethoxyphenyl)ethyl, 5-(3,4-dimethoxyphenyl)pentyl, 2,3-dichlorobenzyl, 3,4-dichlorobenzyl, 3,4,5-trichlorobenzyl, 2,4-dibromobenzyl, 3,4-diiodobenzyl, 3,4-difluorobenzyl, 2-chloro-3-bromobenzyl, 2-(2,3-dichlorophenyl)ethyl, 2-(3,4,5-trichlorophenyl)ethyl, 2-(3,4-dibromophenyl)ethyl, 2-(2,4-diiodophenyl)ethyl, 1-(3,4-dichlorophenyl)ethyl, 1-(3,4,5-tribromophenyl)ethyl, 3-(2,4-dichlorophenyl)propyl, 3-(3,4-dibromophenyl)propyl and 5-(3,4-dichloropheny)pentyl groups and the like.

The expression "a lower alkoxy group" means a straight chain or branched chain alkoxy group having 1 to 6 carbon atoms, and the examples including methoxy, ethoxy, propoxy, isopropoxy, butoxy, tert-butoxy, pentyloxy and hexyloxy groups and the like.

The expression "a halogen atom" means a fluorine, chlorine, brommine and iodine atoms.

The expression "a lower alkylthio group" means a straight chain or branched chain alkylthio group having 1 to 6 carbon atoms, and the examples including methylthio, ethylthio, propylthio, isopropylthio, butylthio, tert-butylthio, pentylthio and hexylthio group and the like.

The expression "a lower alkylenedioxy group" means a straight chain or branched chain alkylenedioxy group having 1 to 4 carbon atoms, and the examples including methylenedioxy, ethylenedioxy and trimethylenedioxy groups and the like.

The expression "5- or 6-membered saturated heterocyclic ring" formed by $R^2$ and $R^3$ including 1-pyrrolidinyl, 1-piperidyl, morpholino, 1-piperazinyl, 4-methyl-1-piperazinyl, 4-methyl-1-piperidyl, 2-methyl-1-piperidyl, 4-ethyl-1-piperazinyl, 4-propyl-1-piperazinyl, 4-butyl-1-piperazinyl, 4-isopropyl-1-piperazinyl, 4-tert-butyl-1-piperazinyl, 4-sec-butyl-1-piperazinyl, 4-pentyl-1-piperazinyl, 4-hexyl-1-piperazinyl, 4-benzylpyrrolidino, 4-benzyl-1-piperidyl, 3-benzylmorpholino, 4-benzyl-1-piperazinyl, 3-(2-phenylethyl)-1-piperidyl, 4-(1-phenylethyl)-1-piperidyl, 4-(3-phenylpropyl)-1-piperazinyl, 4-(4-phenylbutyl)-1-piperidyl, 3-(6-phenylhexyl)-1-piperidyl and 4-(4-phenylbutyl)-1-piperazinyl groups and the like.

The expression "a lower alkanoylamino group" means an amino group having a straight chain or branched chain alkanoyl group having 1 to 6 carbon atoms as the substituent, and the examples including formylamino, acetylamino, propionylamino, butyrylamino, isobutyrylamino, pentanoylamino, tert-butylcarbonylamino and hexanoylamino groups and the like.

The expression "a cycloalkyl group" means a cycloalkyl group having 3 to 8 carbon atoms, and the examples including cyclopropyl, cyclobutyl, cyclopentyl, cyclohexyl, cycloheptyl and cyclooctyl group and the like.

The substituted position of the side chain represented by the formula,

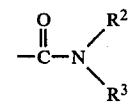

is 5-, 6-, 7- or 8-position in the carbostyril skeleton.

The expression "a benzoyl-lower alkyl group (which may have, on the phenyl ring, 1 to 3 substituents selected from the group consisting of a halogen atom, a hydroxy group, a lower alkyl group, a lower alkoxy group and a lower alkanoylamino group)" means a straight chain or branched chain alkyl group having 1 to 6 carbon atoms, to which a benzoyl group is attached, said benzoyl group may have, on the phenyl ring, 1 to 3 substituents selected from the group consisting of a halogen atom, a hydroxy group, a straight chain or branched chain alkyl group having 1 to 6 carbon atoms, a straight chain or branched chain alkoxy group having 1 to 6 carbon atoms, a straight chain or branched chain alkanoylamino group having 1 to 6 carbon atoms in the alkyl moiety, and the examples including benzoylmethyl, 2-benzoylethyl, 3-benzoylpropyl, 6-benzoylhexyl, 4-benzoylbutyl, (2-methoxybenzyl)methyl, (3-methoxybenzyl)methyl, 2-(4-methoxybenzoyl)ethyl, 2-ethoxybenzoylmethyl, 1-(3-ethoxybenzoyl)ethyl, 3-(4-ethoxybenzoyl)propyl, 6-(4-isopropoxybenzoyl)hexyl, 4-(4-hexyloxybenzoyl)butyl, 1,1-dimethyl-2-(3,4-dimethoxybenzoyl)ethyl, 5-benzoylpentyl, 5-(3,4-diethoxybenzoyl)pentyl, 6-(3,4,5-trimethoxybenzoyl)hexyl, 2-methyl-3-(2,5-dimethoxybenzoyl)propyl, (2-chlorobenzoyl)methyl, (3-bromobenzoyl)methyl, (4-iodobenzoyl)methyl, 2-(4-fluorobenzoyl)ethyl, 1-(3-chlorobenzoyl)ethyl, 6-(4-bromobenzoyl)hexyl, 5-(3,4-dichlorobenzoyl)pentyl, 1,1-dimethyl-2-(2,5-dibromobenzoyl)propyl, (3,4,5-trichlorobenzoyl)methyl, (2-methylbenzoyl)methyl, (3-methylbenzoyl)methyl, 2-(4-methylbenzoyl)ethyl, (2-ethylbenzoyl)methyl, 1-(3-ethylbenzoyl)ethyl, 3-(4-ethylbenzoyl)propyl, 6-(4-isopropylbenzoyl)hexyl, 4-(4-hexylbenzoyl)butyl, 1,1-dimethyl-2-(3,4-dimethylbenzoyl)ethyl, 5-(3,4-diethylbenzoyl)pentyl, 6-(3,5-dimethylbenzoyl)hexyl, 2-methyl-3-(2,5-dimethylphenoxy)propyl, (2-acetylaminobenzoyl)methyl, (3-formylaminobenzoyl)methyl, 1-(3-propionylaminobenzoyl)ethyl, 6-(4-n-butyrylaminobenzoyl)hexyl, 2-(5-pentanoylaminobenzoyl)ethyl, 4-(6-hexanoylaminobenzoyl)butyl, (2-hydroxybenzoyl)methyl, (3-hydroxybenzoyl)methyl, (4-hydroxybenzoyl)methyl, 2-(4-hydroxybenzoyl)ethyl, 1-(3-hydroxybenzoyl)ethyl, 6-(4-hydroxybenzoyl)hexyl, 5-(3,4-dihydroxybenzoyl)pentyl, 1,1-dimethyl-2-

(2,5-dihydroxybenzoyl)propyl and (3,4,5-trihydroxybenzoyl)methyl groups and the like.

The expression "a phenyl-lower alkanoyl group (which may have, on the phenyl ring, 1 to 3 lower alkoxy groups as the substituents)" means an alkanoyl group having 2 to 6 carbon atoms, to which a phenyl group is attached, said phenyl group may have 1 to 3 straight chain or branched chain alkoxy groups having 1 to 6 carbon atoms as the substituents, and the examples including phenylacetyl, 3-phenylpropionyl, 2-phenylpropionyl, 4-phenylbutyryl, 2,2-dimethyl-3-phenylpropionyl, 5-phenylpentanoyl, 6phenylhexanoyl, 3-methyl-4-phenylbutyryl, (2-methoxyphenyl)acetyl, (3-methoxyphenyl)acetyl, (4-methoxyphenyl)acetyl, (3-ethoxyphenyl)acetyl, (2-propoxypheny)acetyl, (3-isopropoxyphenyl)acetyl, (4-tert-butoxyphenyl)acetyl, 3-(3-methoxyphenyl)propionyl, 3-(4-methoxyphenyl)propionyl, 3-(2-ethoxyphenyl)propionyl, 3-(3-butoxyphenyl)propionyl, 4-(2-methoxyphenyl)butyryl, 3-methyl-4-(4-methoxyphenyl)butyryl, 6-(4-methoxyphenyl)hexanoyl, (2,3-dimethoxyphenyl)acetyl, (2,4-dimethoxyphenyl)acetyl, (3,4,5-trimethoxyphenyl)acetyl, (2,4-diethoxyphenyl)acetyl, 3-(3,4-diethoxyphenyl)propionyl, 3-(3,4,5-trimethoxyphenyl)propionyl, 4-(2,3-dimethoxyphenyl)butyryl, 4-(3-methoxy-4-ethoxyphenyl)butyryl, 2,2-dimethyl-3-(3,4,5-trimethoxyphenyl)propionyl and 6-(3,4-dimethoxyphenyl)hexanoyl groups and the like.

The expression "a lower alkyl group which may have hydroxy groups(s) or halogen atom(s) as the substituent(s)" means a straight chain or branched chain alkyl group having 1 to 6 carbon atoms which may have, as the substituent(s), hydroxy group(s) or halogen atoms(s), and the examples including chloromethyl, boromomethyl, iodomethyl, fluoromethyl, 2-chloroethyl, 2-bromoethyl, 2-chloropropyl, 3-chloropropyl, 2-fluoropropyl, 3-iodopropyl, 1-methyl-2-chloroethyl, 2-bromobutyl, 3-bromobutyl, 4-bromobutyl, 3-chlorobutyl, 2-iodobutyl, 4-fluorobutyl, 1,1-dimethyl-2-chlorobutyl, 2-chloropentyl, 3-chloropentyl, 4-bromohexyl, 6-chlorohexyl, 5-bromopentyl, hydroxymethyl, 2-hydroxyethyl, 2-hydroxypropyl, 2-hydroxybutyl, 3-hydroxypropyl, 4-hydroxybutyl, 3-hydroxybutyl, 5-hydroxypentyl and 6-hydroxyhexyl groups and the like.

The expression "a phenyl-lower alkenylcarbonyl group (which may have, on the phenyl ring, 1 to 3 substituents selected from the group consisting of a halogen atoms and a lower alkoxy group)" means a straight chain or branched chain alkenylcarbonyl group having 3 to 6 carbon atoms, to which a phenyl group is attached, said phenyl group may have 1 to 3 substituents selected from the group consisting of a halogen atom, a lower alkoxy group having 1 to 6 carbon atoms, and the examples including cinnamoyl, 4-phenyl-3-butenoyl, 4-phenyl-2-butenoyl, 5-phenyl-4-pentenoyl, 5-phenyl-3-pentenoyl, 5-phenyl-2-pentenoyl, 6-phenyl-5-hexenoyl, 6-phenyl-4-hexenoyl, 6-phenyl-3-hexenoyl, 6-phenyl-2-hexenoyl, 2-methyl-4-phenyl-3-butenyl, 2-methylcinnamoyl, 1-methylcinnamoyl, 2-chlorocinnamoyl, 3-chlorocinnamoyl, 4-chlorocinnamoyl, 2-fluorocinnamoyl, 3-fluorocinnamoyl, 4-fluorocinnamoyl, 2-bromocinnamoyl, 3-bromocinnamoyl, 4-bromocinnamoyl, 2-iodocinnamoyl, 3-iodocinnamoyl, 4-iodocinnamoyl, 3,5-dichlorocinnamoyl, 2,6-dichlorocinnamoyl, 3,4-dichlorocinnamoyl, 3,4-difluorocinnamoyl, 3,5-dibromocinnamoyl, 3,4,5-trichlorocinnamoyl, 4-fluorophenyl-3-butenoyl, 4-(3-chlorophenyl)-2-butenoyl, 5-(4-bromophenyl)-4-pentenoyl, 6-(3,4-dichlorophenyl)-5-hexenoyl, 2-methyl-(2,5-dibromophenyl)cinnamoyl, 1-methyl-(3-chlorophenyl)cinnamoyl, 6-(3,4,5-tribromophenyl)-3-hexenoyl, 2-methoxycinnamoyl, 3-methoxycinnamoyl or 4-methoxycinnamoyl, 2-ethoxycinnamoyl, 3-ethoxycinnamoyl or 4-ethoxycinnamoyl, 2-propoxycinnamoyl, 3-propoxycinnamoyl or 4-propoxycinnamoyl, 2-butoxycinnamoyl, 3-(tert-butoxy)cinnamoyl, 4-pentyloxycinnamoyl, 3-hexyloxycinnamoyl, 3,5-dimethoxycinnamoyl, 2,6-dimethoxycinnamoyl, 3,4-dimethoxycinnamoyl, 3,4-diethoxycinnamoyl, 3,5-diethoxycinnamoyl, 3,4,5-trimethoxycinnamoyl, 4-ethoxyphenyl-3-butenoyl, 4-(3-tert-butoxyphenyl)-2-betenoyl, 5-(4-hexyloxyphenyl)-4-pentenoyl, 6-(3,4-dimethoxyphenyl)-5-hexenoyl, 2-methyl-(2,5-diethoxyphenyl)cinnamoyl, 1-methyl-(3-methoxyphenyl)cinnamoyl, and 6-(3,4,5-triethoxyphenyl)-3-hexenyl groups and the like.

The expression "a lower alkanoyl-lower alkyl group" means a straight chain or branched chain alkyl group having 1 to 6 carbon atoms, to which a straight chain or branched chain alkanoyl group having 1 to 6 carbon atoms is attached, and the examples including acetylmethyl, 2-acetylethyl, 2-acetylpropyl, 3-acetylpropyl, 4-acetylbutyl, 3-acetylbutyl, 5-acetylpentyl, 6-acetylhexyl, 2-propionylethyl, 3-formylpropyl, 2-butyrylpropyl, 4-isobutyrylbutyl, 2-pentanoylethyl, tert-butylcarbonylmethyl, 2-hexanoylethyl and 1,1-dimethyl-2-acetylethyl groups and the like.

The expression "a lower alkoxycarbonyl-lower alkyl group" means a straight chain or branched chain alkyl group having 1 to 6 carbon atoms, to which a straight chain or branched chain alkoxycarbonyl group having 1 to 6 carbon atoms is attached, and the examples including methoxycarbonylmethyl, 2-(methoxycarbonyl)ethyl, ethoxycarbonylmethyl, 1-(ethoxycarbonyl)ethyl, 3-(methoxycarbonyl)propyl, propoxycarbonylmethyl, 2-(propoxycarbonyl)methyl, 4-(propoxycarbonyl)butyl, butoxycarbonylmethyl, 1-(butoxycarbonyl)ethyl, tert-butoxycarbonylmethyl, 3-(tert-butoxycarbonyl)propyl, pentyloxycarbonylmethyl, 2-(hexyloxycarbonyl)ethyl, 5-(methoxycarbonyl)pentyl and 6-(ethoxycarbonyl)hexyl groups and the like.

Carbostyril derivatives of the present invention can be prepared according to various processes such as for example expressed by the following reaction process formula-1:

REACTION PROCESS FORMULA-1

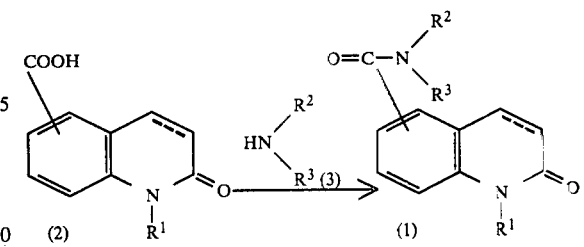

wherein $R^1$, $R^2$, $R^3$ and the carbon-carbon bond between 3- and 4-positions in the carbostyril skeleton are the same as defined previously.

According to reaction process formula-1, carbostyril derivative represented by the general formula (1) can be prepared by reacting a known carboxylic acid derivative or its carboxylic group-activated compound represented by the general formula (2) with an amine or its amino group-activated compound represented by the general formula (3) under a conventional amide bond forming reaction condition.

As to the amide bond forming reaction condition, the following methods can be exemplified, for example, (a) mixed acid anhydride method: e.g., a method by reacting a carboxylic acid (2) with an alkyl halocarboxylic acid to form a mixed acid anhydride, then the mixed acid anhydride is reacted with an amine (3); (b) activated ester method: e.g., a method by reacting an activated ester of a carboxylic acid (2), for example p-nitrophenyl ester, N-hydroxysuccinimide ester, 1-hydroxybenzotriazol ester, with an amine (3); (c) carbodiimide method: e.g., a method by dehydro-condensing a carboxylic acid (2) with an amine (3) in the presence of a dehydrating agent, for example, dicyclohexylcarbodiimide, carbonylidiimidazol or the like; (d) carboxylic acid halide method: e.g., a method by changing a carboxylic acid (2) into an acid halide form, then the halide of carboxylic acid (2) is reacted with an amine (3); (e) a method by reacting a carboxylic acid (2) with a dehydrating agent, for example, acetic anhydride, to obtain a carboxylic acid anhydride, then the carboxylic acid anhydride is reacted with an amine (3); (f) a method by reacting an ester of a carboxylic acid (2), being prepared from it with a lower alcohol, with an amine (3) under a high pressure and high temperature condition; (g) a method by activating a carboxylic acid (2) with a phosphorus compound, for example, triphenylphosphine or diethylchlorophosphate, said activated compound of carboxylic acid (2) is reacted with an amine (3).

In the mixed acid anhydride method (a), the mixed acid anhydride is obtained by a conventional Schotten-Baumann reaction, and generally the mixed acid anhydride is reacted with an amine (3), without being separated from the reaction mixture of Schotten-Baumann reaction, to obtain carbostyril derivative (1) of the present invention. The Schotten-Baumann reaction is carried out in the presence of a basic compound, for example, an organic basic compound such as triethylamine, trimethylamine, pyridine, dimethylaniline, N-methylmorpholine, 4-dimethylaminopyridine, 1,5-diazabicyclo[4,3,0]nonene-5 (DBN), 1,5-diazabicyclo[5,4,0]undecene-5 (DBU), 1,4-diazabicyclo[2,2,2]octane (DABCO) or the like, an inorganic basic compound, such as potassium carbonate, sodium carbonate, potassium hydrogencarbonate, sodium hydrogencarbonate or the like, at a temperature about $-20°$ to $100°$ C., preferably, at $0°$ to $50°$ C., for about 5 minutes to 10 hours, preferably, for 5 minutes to 2 hours. Reaction of the thus obtained mixed acid anhydride with an amine (3) is carried out at a temperature of $-20°$ to $150°$ C., preferably, at $10°$ to $50°$ C., for about 5 minutes to 10 hours, preferably, for 5 minutes to 5 hours.

The above-mentioned mixed acid anhydride method is generally carried out in the absence or presence of a suitable solvent usually used for this type of mixed acid anhydride method, concretely a halogenated hydrocarbon for example, methylene chloride, chloroform, dichloroethane or the like, an aromatic hydrocarbon for example, benzene, toluene, xylene or the like, an ether for example, diethyl ether, tetrahydrofuran, dimethoxyethane or the like, an ester for example, methyl acetate, ethyl acetate or the like, an aprotic polar solvent for example, N,N-dimethylformamide, dimethyl sulfoxide, hexamethylphosphoric triamide or the like can be exemplified.

As to the alkylhalocarboxylic acid used for preparing above-mentioned mixed acid anhydride can be exemplified such as methyl chloroformate, methyl bromoformate, ethyl chloroformate ethyl bromoformate, isobutyl chloroformate or the like, and generally said alkylhalocarboxylic acid is used in at least an equimolar amount, preferably, 1 to 2 times the molar quantity of the carboxylic acid (2). The amine (3) is generally used in at least an equmolar amount, preferably 1 to 2 times the molar quantity of the carboxylic acid (2).

The activated ester method as mentioned (b) as above, for example, in using N-hydroxysuccinimide ester, the reaction is generally carried out in a suitable inert solvent. As to the solvent, concretely a halogenated hydrocarbon for example, methylene chloride, chloroform, dichloroethane or the like, an aromatic hydrocarbon for example, benzene, toluene, xylene or the like, an ether for example, diethyl ether, terahydrofuran, dimethoxyethane or the like, an ester for example, methyl acetate, ethyl acetate or the like, an aprotic polar solvent for example, N,N-dimethylformamide, dimethyl sulfoxide, hexamethylphosphoric triamide or the like can be exemplified.

The reaction is carried out at a temperature of $0°$ to $150°$ C., preferably, at $10°$ to $100°$ C., for 5 to 30 hours.

The amine (3) is usually used in an equimolar amount, preferably 1 to 2 times the molar quantity of the N-hydroxysuccinimide ester.

In the carboxylic acid halide method (d) as above, that is by reacting a carboxylic acid halide with an amine (3), the reaction can be carried out in a suitable solvent in the presence of a dehydrohalogenating agent. As to the dehydorhalogenating agent, a common basic compound which is known widely can be used, for example, a basic compound used in the above-mentioned Schotten-Baumann reaction can also be used, additionally sodium hydroxide, potassium hydroxide, sodium hydride, potassium hydride, silver carbonate, an alcoholate, for example, sodium methylate or sodium ethylate can be exemplified. Said dehydrohalogenating agent is used with an excess amount of an amine (3). As to the solvent used in the carboxylic acid halide method, any solvent used in the above-mentioned Schotten-Baumann resction can also be used, further an alcohol such as, methanol, ethanol, propanol, butanol, 3-methoxy-1-butanol, ethyl cellosolve, methyl cellosolve or the like, pyridine, acetone, acetonitrile or the like or a mixture of the solvents in combination of two or more of the above-mentioned solvents can also be exemplified.

There is not any specific restriction to the ratio of the amount of an amine (3) to the amount of a carboxylic acid halide in the above reaction, the ratio can be selected from a wide range, and the latter may be used at least in an equimolar amount, preferably an equimolar to 2 times the molar quantity to the former.

The reaction is generally carried out at a temperature of $-30°$ to $180°$ C., preferably at about $0°$ to $150°$ C., and the reaction is completed for 5 minutes to 30 hours.

The carboxylic acid halide used in this reaction can be prepared by reacting a carboxylic acid (2) with a halogenating agent in the absence or presence of a solvent. As to the solvent, any solvent which does not give adverse effect to the reaction can be used, for example an aromatic hydrocarbon such as benzene, toluene, xylene or the like, a halogenated hydrocarbon such as chloroform, methylene chloride, carbon tetrachloride or the like, an ether such as dioxane, tetrahydrofuran, diethyl ether or the like, dimethylformamide, dimethyl sulfoxide or the like can be exemplified. As to the halogenating agent, a common halogenating agent which changes hydroxy group in the carboxyl group can be used, for example thionyl chloride, phosphorus oxychloride, phosphorus oxybromide, phosphorus pentachloride, phosphorus pentabrimide or the like can be exemplified.

There is not any specific restriction to the ratio of the amount of a carboxylic acid (2) to the amount of a halogenating agent in the reaction, the ratio can be selected from a wide range, when the reaction is carried out in the absence of a solvent, the latter is used in an excess amount to the former, and when the reaction is carried out in the presence of a solvent, the latter is used at least in an equimolar amount, preferably, 2 to 4 times the molar quantity to the former. The reaction temperature (and the reaction time) may not be restricted, and generally the reaction can be carried out at a room temperature to 100° C., preferably 50° to 80° C., for 30 minutes to 6 hours.

In the method (g) by activating a carboxylic acid (2) with a phosphorus compound, for example, triphenylphosphine or diethylchlorophosphate, then said activated compound of carboxylic acid (2) is reacted with an amine (3), the reaction can be carried out in a suitable solvent. As to the solvent, any solvent which does not give adverse effect to the reaction can be used, concretely for example, a halogenated hydrocarbon such as methylene chloride, chloroform, dichloroethane or the like, an aromatic hydrocarbon, such as benzene, toluene, xylene or the like, an ether such as diethyl ester, tetrahydrofuran, dimethoxyethane or the like, an ester such as methyl acetate, ethyl acetate or the like, an aprotic polar solvent such as N,N-dimethylformamide, dimethyl sulfoxide, hexamethylphosphoric triamide or the like can be exemplified.

In this reaction, since an amine (3) per se performs as a basic compound, the reaction can be proceeded smoothly, and further, if necessary other basic compound, for example an organic basic compound such as triethylamine, trimethylamine, pyridine, dimethylaniline, N-methylmorpholine, DBN, DBU, DABCO or the like, an inorganic basic compound, such as potassium carbonate, sodium carbonate, potassium hydrogencarbonate, sodium hydrogencarbonate or the like can be used.

The reaction can be carried out at a temperature of about 0° to 150° C., preferably at about 0° to 100° C., and the reaction time is about 1 to 30 hours. The ratio of the amounts of a phosphorus compound and an amine (3) to the amount of a carboxylic acid (2) is generally at least in an equimolar quantity, preferably 1 to 3 times the molar quantity.

Among the carbostyril derivatives of the present invention, compounds represented by the general formulas (1-a), (1-b) and (1-c) can be prepared, respectively by methods according to reaction process formulas-2 to -5 as follows:

REACTION PROCESS FORMULA-2

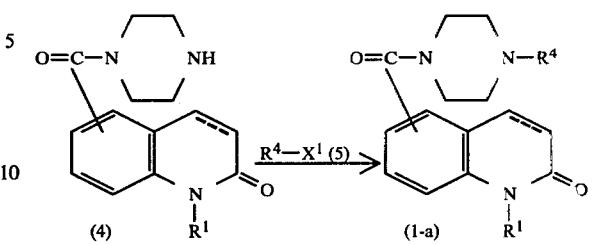

wherein $R^1$ and the carbon-carbon bond between 3- and 4-positions in the carbostyril skeleton are the same as defined previously; $R^4$ is a lower alkanoyl group, a lower alkoxycarbonyl group, a furoyl group, a benzoyl group (which may have, on the phenyl ring, 1 to 3 substituents selected from the group consisting of a lower alkyl group, a lower alkoxy group, a halogen atom, a nitro group and a cyano group, or said benzoyl group may have, on the phenyl ring, a lower alkylenedioxy group as the substituent), a phenyl-lower alkanoyl group (which may have, on the phenyl ring, 1 to 3 lower alkoxy group as the substituents) or a phenyl-lower alkenylcarbonyl group (which may have, on the phenyl ring, 1 to 3 substituents selected from the group consisting of a halogen atom and a lower alkoxy group); $X^1$ is a hydroxyl group.

A compound represented by the general formula (1-a) of the present invention can be prepared by reacting a compound (4) or an activated compound of its amino group, with a compound (5) or an activated compound of its carboxyl group. The above-mentioned reaction can be carried out by a procedure and under conditions similar to those mentioned in the reaction of a compound (2) or an activated compound of its carboxyl group, with an amine derivative (3) or an activated compound of its amino group, used in reaction process formula-1.

REACTION PROCESS FORMULA-3

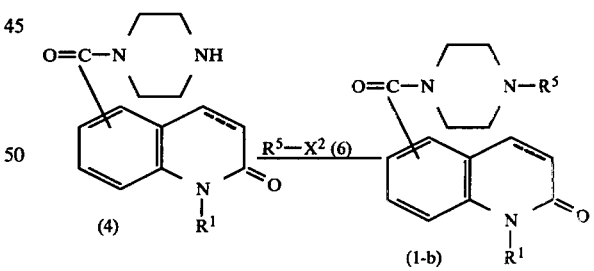

wherein $R^1$ and the carbon-carbon bond between 3- and 4-positions in the carbostyril skeleton are the same as defined as previously; $R^5$ is a lower alkyl group, a lower alkoxycarbonyl-lower alkyl group, a lower alkenyl group, a lower alkynyl group, cycloalkyl group, a cycloalkyl-lower alkyl group, a lower alkylsulfonyl group, a phenoxy-lower alkyl group (which may have, on the phenyl ring, 1 to 3 substituents selected from the group consisting of a halogen atom, a lower alkoxy group and a lower alkyl group, or said phenoxy-lower alkyl group may have, on the phenyl ring, a lower alkylenedioxy group as the substituent), a substituted lower alkyl group (having one substituent selected from the group consisting of a cyano group, a benzoyloxy group (which may have 1 to 3 lower alkoxy groups on the phenyl ring), a hydroxy group a lower alkanoyloxy group, a halogen atom and a carbamoyl group), a lower alkanoyl-lower alkyl group, a phenyl-lower alkyl group (which may have, on the phenyl ring, 1 to 3 lower alkyl groups as the substuents) or a benzoyl-lower alkyl group (which may have, on the phenyl ring, 1 to 3 substituents selected from the group consisting of a halogen atom, a hydroxy group, a lower alkyl group, a lower alkoxy group and a lower alkanoylamino group); $X^2$ is a halogen atom, a lower alkanesulfonyloxy group, an arylsulfonyloxy group or an aralkylsulfonyloxy group.

Carbostyril derivative represented by the general formula (1-b) can be prepared by reacting a compound represented by the general formula (4) with a compound represented by the general formula (6). This reaction can be carried out by procedures under the conditions similar to those described in the reaction of carboxylic acid halide with an amine (3) as mentioned above.

In the compound represented by the general formula (6), in the definitions for the symbol $X^2$, the halogen atom is specifically a chlorine, fluorine, bromine or iodine atom; the lower alkanesulfonyloxy group can be exemplified such as methanesulfonyloxy, ethanesulfonyloxy, isopropanesulfonyloxy, propanesulfonyloxy, butanesulfonyloxy, tert-butanesulfonyloxy, pentanesulfonyloxy, hexanesulfonyloxy or the like; the arylsulfonyloxy group is specifically a substituted or unsubstituted arylsulfonyloxy group such as phenylsulfonyloxy, 4-methylphenylsulfonyloxy, 2-methylphenylsulfonyloxy, 4-nitrophenylsulfonyloxy, 4-methoxyphenylsulfonyloxy, 3-chlorophenylsulfonyloxy, α-naphthylsulfonyloxy group or the like; the aralkylsulfonyloxy group is specifically a substituted or unsubstituted aralkylsulfonyloxy group such as benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy, α-naphthylmethylsulfonyloxy group or the like.

REACTION PROCESS FORMULA-4

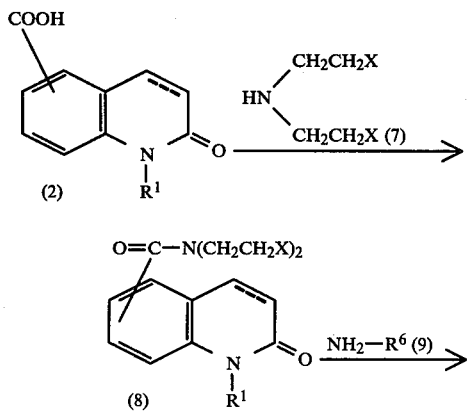

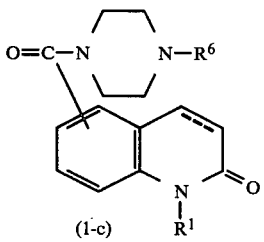

wherein $R^1$ and the carbon-carbon bond between 3- and 4-positions in the carbostyril skeleton are the same as defined previously; $R^6$ is a lower alkyl group, a lower alkoxycarbonyl-lower alkyl group, a lower alkenyl group, a lower alkynyl group, a cycloalkyl group, a cycloalkyl-lower alkyl group, a phenoxy-lower alkyl group (which may have, on the phenyl ring, 1 to 3 substituents selected from the group consisting of a halogen atom, a lower alkoxy group and a lower alkyl group, or said phenoxy-lower alkyl group may have, on the phenyl ring, a lower alkylenedioxy group as the substituent) a substituted lower alkyl group (having one substituent selected from the group consisting of a cyano group, a benzoyloxy group (which may have 1 to 3 lower alkoxy groups on the phenyl ring), a hydroxy group, a lower alkanoyloxy group, a halogen atom and a carbamoyl group), a lower alkanoyl-lower alkyl group, a phenyl-lower alkyl group (which may have, on the phenyl ring, 1 to 3 substituents selected from the group consisting of a lower alkyl group, a lower alkoxy group, a halogen atom, a nitro group, an amino group, a lower alkanoylamino group and a lower alkylthio group, or said phenyl-lower alkyl group may have, on the phenyl ring, a lower alkylenedioxy group as the substituent) or a benzoyl-lower alkyl group (which may have, on the phenyl ring, 1 to 3 substituents selected from the group consisting of a halogen atom, a hydroxy group, a lower alkyl group, a lower alkoxy group and a lower alkanoylamino group), X is the same as defined in $X^1$ and $X^2$.

A compound represented by the general formula (1-c) of the present invention can be prepared by reacting a compound of the general formula (2) with a compound of the general formula (7) to obtain a compound of the general formula (8), then reacting a compound of the general formula (8) with a compound of the general formula (9). The reaction in the above-mentioned first step is carried out by procedure under the conditions similar to those described in the reaction of a compound of the general formula (2) with a compound of the general formula (3). The reaction in the second step followed by the above-mentioned first step can be carried out the following procedure according to the type of X in the general formula (8). Thus, when a compound of the general formula (8) wherein X is a halogen atom, a lower alkanesulfonyloxy group, an arylsulfonyloxy group or an aralkylsulfonyloxy group, is used, the reaction of a compound of the general formula (8) with a compound of the general formula (9) is carried out in a suitable incert solvent in the absence or presence of a basic condensing agent. As to the inert solvent, an aromatic hydrocarbon for example benzen, toluene, xylene or the like, a lower alcohol for example methanol, ethanol, isopropanol, butanol or the like, acetic acid, ethyl acetate, dimethyl sulfoxide, dimethylformamide, hexamethylphosphoryl triamide or the like can be exemplified. As to the basic condensing agent, a carbonate for example potassium carbonate, sodium hydrogencarbonate, potassium hydrogencarbonate or the like, a metal hydroxide for example sodium hydroxide, potassium hydroxide or the like, a metal alcoholate for example sodium methylate, sodium ethylate or the like, a tertiary amine for example pyridine, triethylamine or the like can be exemplified.

There is not any specific restriction to the ratio of the amount of a compound of the general formula (8) to the amount of a compound of the general formula (9) in the above reaction, and the ratio can suitably be selected from a wide range, generally the latter may be used at least in a equimolar amount, preferably an equimolar to 5 times the molar quantity to the former.

The reaction is carried out generally at 40° to 120° C., preferably 50° to 100° C., and the reaction is completed within about 5 to 30 hours.

On the other hand, when a compound of the general formula (8) wherein X is a hydroxy group is used, the reaction of a compound of general formula (8) with a compound of the general formula (9) is carried out in the presence of a dehydrating-condensing agent in the absence or presence of a suitable solvent. As to the dehydrating-condensing agent, a condensed phosphoric acid for example a polyphosphoric acid or the like, a phosphoric acid for example orthophosphoric acid, pyrophosphoric acid, metaphosphoric acid or the like, a phosphorous acid for example orthophosphorous acid or the like, a phosphoric acid anhydride for example phosphorus pentoxide, an acid for example hydrochloric acid, sulfuric acid, boric acid or the like, a metal phosphate for example sodium phosphate, boron phosphate, ferric phosphate, aluminium phosphate or the like, activated alumina, sodium bisulfate, Raney nickel or the like can be exemplified. As to the solvent a high boiling point solvent for example dimethylformamide, tetrahydronaphthalene or the like can be exemplified.

There is not any specific restriction to the ratio of the amount of a compound of the general formula (8) to the amount of a compound of the general formula (9) in the above reaction, and the ratio can suitably be selected from a wide range, generally the former may be used in 0.8 times the molar quantity or more, preferably 0.8 to 2 times the molar quantity. There is not any specific restriction to the amount of the dehydrating-condensing agent, and the amount can be selected suitably from a wide range, and generally a catalytic amount or more, preferably 0.5 to 5 times the molar quantity of the dehydrating-condensing agent can be used to the equimolar quantity of a compound of the general formula (8).

The reaction can advantageously be carried out in an inert gas stream for example in $CO_2$ or $N_2$ gas stream for the purpose of to prevent oxidation reaction. The reaction is generally carried out under a normal pressure at about 100° to 350° C., preferably at 125° to 255° C. for about 3 to 10 hours.

REACTION PROCESS FORMULA-5

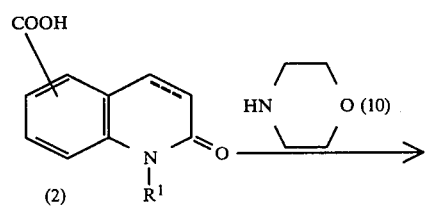

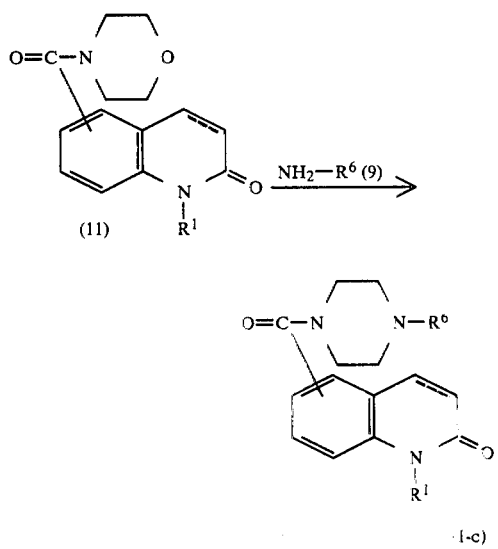

wherein $R^1$, $R^6$ and the carbon-carbon bond between 3- and 4-positions in the carbostyril skeleton are the same as defined previously.

A compound represented by the general formula (1-c) of the present invention can also be prepared by reacting a compound of the general formula (2) with morpholine (10) to obtain a morpholine derivative (11), then reacting the morpholine derivative (11) with a compound of the general formula (9).

The reaction of a compound of the general formula (2) with morpholine (10) can be carried out by a procedure under the conditions similar to those described in the reaction of a compound of the general formula (2) with a compound of the general formula (3). The reaction of the obtained compound of the general formula (11) with a compound of the general formula (9) is carried out in the presence of an acid in the absence or presence of a suitable solvent. As to the solvent, a high boiling point solvent such as tetrahydronaphthalene, dimethyl sulfoxide, dimethylformamide, hexamethylphosphoric triamide or the like can be used. As to the acid, hydrochloric acid, sulfuric acid, hydrobromic acid or the like can be used. There is not any specific restriction to the ratio of the amount of a compound of the general formula (11) to the amount of a compound of the general formula (9), and the ratio can suitably be selected from a wide range, generally, the latter may be used at least in an equimolar quantity, preferably an equimolar to 2 times the molar quantity to the former. The reaction is generally carried out at 50° to 250° C., preferably at 150° to 200° C., and the reaction is completed within about 1 to 24 hours.

Among the compounds of the general formula (1) of the present invention, those having substituent other than hydrogen as for the symbol $R^1$ (a compound of the general formula (1-e) can be prepared from a compound having a hydrogen atom as for the symbol $R^1$ (a compound of the general formula (1-d)) by a method as described in reaction process formula-6 as follows:

REACTION PROCESS FORMULA-6

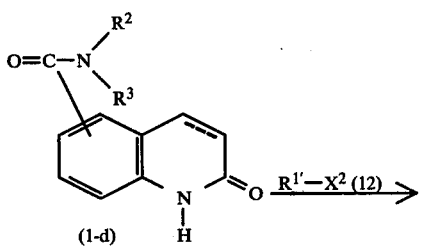

(1-d)

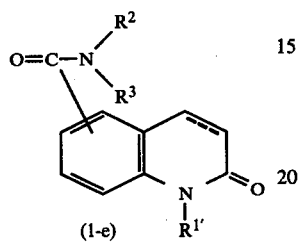

(1-e)

wherein $R^2$, $R^3$, $X^2$ and the carbon-carbon bond between 3- and 4-positions in the carbostyril skeleton are the same as defined previously; $R^{1'}$ is the same as the definition of $R^1$ excluding a hydrogen atom.

The reaction of a compound of the general formula (1-d) with a compound of the general formula (12) may be carried out in a suitable solvent in the presence of a basic compound. As to the basic substance, sodium hydride, potassium metal, sodium metal, sodium amide, potassium amide, or the like can be exemplified. As to the solvent, an ether such as dioxane, diethylene glycol dimethyl ether or the like, an aromatic hydrocarbon such as toluene, xylene or the like, dimethylformamide, dimethyl sulfoxide, hexamethylphosphoric triamide or the like can be exemplified.

There is not any specific restriction to the ratio of the amount of a compound of the general formula (1-d) to the amount of a compound of the general formula (12) in the above reaction, and the ratio can suitably be selected from a wide range, generally the latter may be used at least in an quimolar quantity or more, preferably an equimolar to 2 times the molar quantity to the former. The reaction is generally carried out at 0° to 70° C., preferably at 0° C. to a room temperature and the reaction is completed within 0.5 to 12 hours.

Among the compounds represented by the general formula (1), those having amino group as the substituent on the phenyl ring can easily be prepared by reducing the corresponding compound having nitro group as the substituent on the phenyl ring. This reducing reaction can be carried out under the conditions generally used in reducing an aromatic nitro compound to the corresponding aromatic amino compound. More specifically, the reducing reaction can be carried out by a method using sodium sulfite or sulfur dioxide as a reducing agent, or a catalytic reducing method using a palladium-carbon or the like as a reducing catalyst.

In the reaction process formulas-1, -4 and -5 as explained in detail as above, compounds of the general formula (2), being used for preparing the objective carbostyril derivative, partially including novel compounds and said compound of the general formula (2) can be prepared by a method according to reaction process formulas-7 or -8 as follows:

REACTION PROCESS FORMULA-7

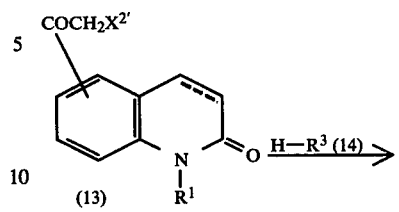

(13)

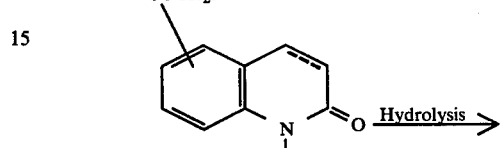

(15)

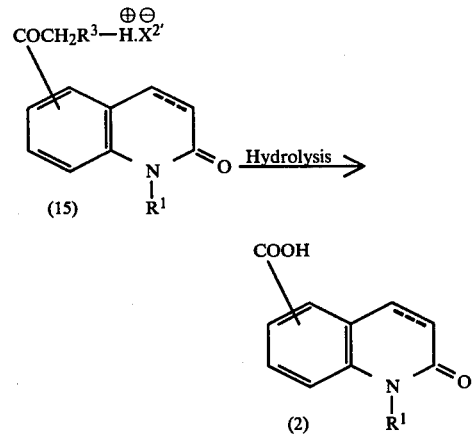

(2)

wherein $R^1$ and the carbon-carbon bond between 3- and 4-position in the carbostyril skeleton are the same as defined previously; $R^3$—H is an aromatic amine; and $X^{2'}$ is a halogen atom.

The reaction for obtaining a compound of the general formula (15) can be carried out in the absence or presence of a suitable solvent by reacting a compound of the general formula (13) with an aromatic amine (14). As to the solvent, any solvent which does not give adverse effect can be used, for example a halogenated hydrocarbon such as methylene chloride, chloroform, dichloromethane or the like, an ether such as diethyl ether, tetrahydrofuran, dimethoxyethane or the like, an ester such as methyl acetate, ethyl acetate or the like, an aprotic polar solvent such as N,N-dimethylformamide, dimethyl sulfoxide, hexamethylpohosphoric triamide or the like can be exemplified. As to the aromatic amine, pyridine, quinoline or the like can be exemplified. The amount of the aromatic amine to be used is at least in an equimolar amount, preferably a great excess amount may be used to the compound of the general formula (13). The reaction temperature is 50° to 200° C., preferably 70° to 150° C., and the reaction is completed within 3 to 10 hours. The hydrolysis reaction of a compound of the general formula (15) thus obtained can be carried out in water, by using an inorganic basic compound such as sodium hydroxide or potassium hydroxide, or an acid such as hydrochloric acid or hydrobromic acid, at a room temperature to 150° C. for 1 to 10 hours. The piperazine derivatives represented by the general formula (3) which are used as another starting material in reaction process formula-1 also including partially novel compounds, and these compounds can easily be obtained by using piperazine in place of a compound of the general formula (4) in the reaction of a compound of the general formula (4) with a compound of the general formula (5) or (6).

REACTION PROCESS FORMULA-8

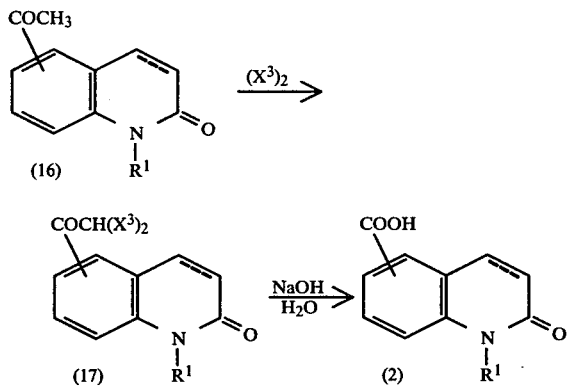

wherein $R^1$ and the carbon-carbon bond between 3- and 4-positions in the carbostyril skeleton are the same as defined previously; $X^3$ is a halogen atom.

The reaction of a compound of the general formula (16) with a halogen is generally carried out in a suitable solvent. As to the solvent to be used, an ether such as tetrahydrofuran, dioxane or the like, a carboxylic acid such as acetic acid, propionic acid or the like, an aromatic hydrocarbon such as benzene or the like, dimethylformamide, dimethyl sulfoxide or the like can be exemplified. In carrying out the reaction, calcium carbonate or the like can be added as an deacidifying agent for removing a hydrogen halide being formed as the by-product.

There is not any specified restriction to the ratio of the amount of a compound of the general formula (17) to the amount of a halogen in this reaction, and the ratio can be suitably selected from a wide range, generally the latter may be used in 2 to 5 times the molar quantity, preferably 2 to 3 times the molar quantity to the former. The reaction may be generally carried out at 0° to 50° C., and is completed within a several hours to 24 hours.

The reaction for obtaining a compound of the general formula (2) from a compound of the general formula (17) may be carried out in an aqueous solvent in the presence of a basic compound. As to the basic compound, a known basic compound can be used for example, alkali metal hydroxide, or a alkaline earth metal hydroxide, such as sodium hydroxide, potassium hydroxide, calcium hydroxide can be exemplified. There is not any specific restriction to the ratio of the amount of a basic compound, and the ratio can be selected from a wide range, generally 2 times the molar quantity or a great excess quantity of the basic compound may be used to the compound of the general formula (17). The reaction may be carried out at 50° to 150° C., preferably 70° to 120° C., and generally the reaction is completed in 1 to 12 hours.

In the reaction process formulas-7 and -8, compounds of the general formulas (13) and (16) being used as the starting materials including novel and known compounds, and they can be prepared respectively by methods according to reaction process formulas-9, -10a, -11a and -11b.

REACTION PROCESS FORMULA-9

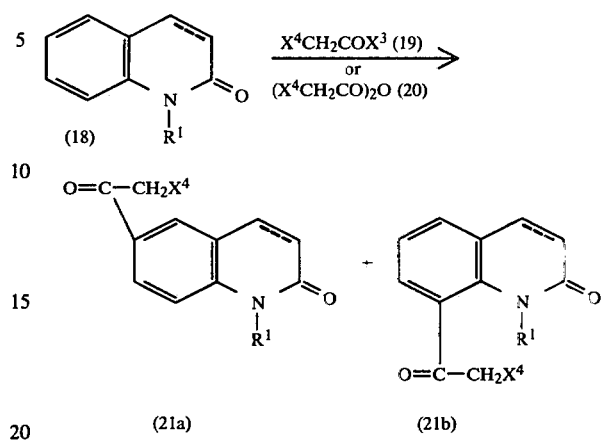

wherein $X^3$ is a halogen atom; $X^4$ is a hydrogen atom or a halogen atom; $R^1$ and the carbon-carbon bond between 3- and 4-positions in the carbostyril skeleton are the same as defined previously.

The reaction of a compound of the general formula (18) with a compound of the general formula (19) or (20) is called generally as Friedel-Crafts reaction and the reaction is carried out in a solvent in the presence of a Lewis acid. As to the solvent to be used in this reaction, any solvent generally used for this reaction can advantageously be used, for example carbon disulfide, nitrobenzene, chlorobenzene, dichloromethane, dichloroethane, trichloroethane, tetrachloroethane or the like can be exemplified. As to the Lewis acid, any Lewis acid generally used for this type of reaction can preferably be used, for example aluminium chloride, zinc chloride, ferric chloride, tin chloride, boron tribromide, boron trifluoride, concentrated sulfuric acid or the like can be used. The amount of Lewis acid being used may suitably be determined and generally 2 to 6 times the molar quantity, preferably 3 to 4 times the molar quantity of Lewis acid is used to a compound of the general formula (18). The amount of a compound of the general formula (19) or (20) to the amount of a compound of the general formula (18) may be of at least an equimolar quantity, preferably an equimolar to 3 times the molar quantity to the latter. The reaction temperature can be suitably selected, and generally 20° to 120° C., preferably 40° to 70° C. The reaction time may be varied depend on the type of the starting materials and the catalyst and the reaction temperature, and generally the reaction can be completed in 0.5 to 24 hours.

REACTION PROCESS FORMULA-10a

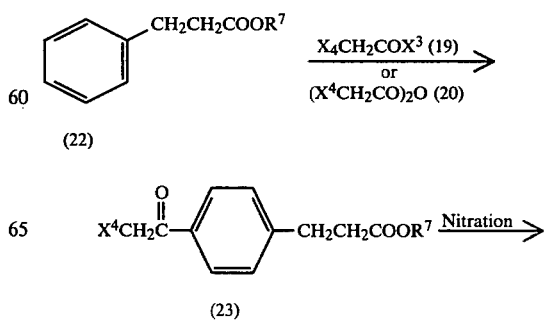

-continued

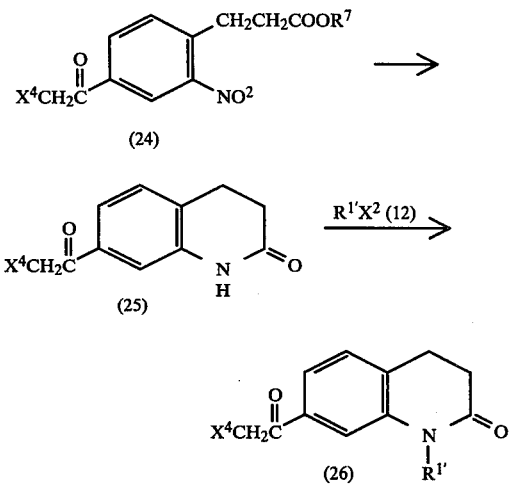

wherein $X^2$ is a halogen atom; $R^{1'}$ is a lower alkyl group, a lower alkenyl group, a lower alkynyl group or a phenyl-lower alkyl group; $R^7$ is a hydrogen atom or a lower alkyl group; $X^3$ and $X^4$ are the same as defined previously.

The reaction of a compound of the general formula (22) with a compound of the general formula (19) or (20) can be carried out by a method similar to that described in the reaction of a compound of the general formula (18) with a compound of the general formula (19) or (20), except the reaction temperature. Thus the reaction may be carried out suitably at within the range of $-50°$ to $120°$ C., preferably at $0°$ to $70°$ C. The reaction time may be varied depend on the type of the starting materails and the catalyst and the reaction temperature, generally the reaction can be completed in 0.5 to 24 hours. The nitration of a compound (23) is generally carried out under conventional conditions of nitration of an aromatic compound in the absence or presence of a suitable inert solvent by using a nitration agent. As to the inert solvent, acetic acid, acetic anhydride and concentrated sulfuric acid can be exemplified. As to the nitration agent, fuming nitric acid, concentrated nitric acid, a mixed acid (a mixture of nitric acid with sulfuric acid, fuming sulfuric acid, phosphoric acid or acetic anhydride), a mixture of an alkali metal nitrate, for example potassium nitrate, sodium nitrate, with sulfuric acid can be exemplified. The amount of the nitration agent to be used may be of an equimolar quantity or excess quantity to the starting material, and the nitration is generally carried out at a temperature within the range of from $-30°$ C. to a room temperature, preferably at about $-30°$ C., for 5 minutes to 4 hours.

The carbostyril compound of the general formula (25) is prepared by reducing and ring closing the compound of the general formula (24). This reaction can be carried out (1) by reducing the compound (24) with a reducing catalyst in a suitable solvent or (2) by reducing the compound (24) in a suitable inert solvent by using a mixture of a metal or a metal salt with an acid, or a mixture of a metal or a metal salt with hydroxide, or sulfide of an alkali metal or ammonium, as a reducing agent. In case of using a method of catalytic reduction (1), as to the solvent, water, acetic acid, an alcohol such as methanol, ethanol, isopropanol or the like, a hydrocarbon such as hexane, cyclohexane or the like, an ether such as diethylene glycol dimethyl ether, dioxane, tetrahydrofuran, diethyl ether or the like, an ester such as ethyl acetate, methyl acetate or the like, an aprotic polar solvent such as dimethylformamide can be exemplified. As to the catalyst, palladium, palladium black, palladium-carbon, platinum, platinum oxide, copper chromite, Raney nickel or the like can be used. The amount of the catalyst to be used may be of 0.02 to 1.00 times the weight of the compound (24). The reduction is carried out at $-20°$ to $100°$ C., preferably $0°$ to $50°$ C., under 1 to 10 atmospheric pressure of hydrogen and the reduction is generally completed in about 0.5 to 10 hours. The catalytic reduction can advantageously be carried out by adding a basic substance such as sodium hydroxide or potassium hydroxide or the like. On the other hand, in case of using a method (2), a mixture of iron, zinc, tin or stannic chloride with a mineral acid such as hydrochloric acid or sulfuric acid, or a mixture of iron, ferrous sulfate, zinc or tin with an alkali metal hydroxide such as sodium hydroxide, a sulfide such as ammonium sulfide, ammonia water, or an ammonium salt such as ammonium chloride, can be used as the reducing agent. As to the solvent to be used, water, acetic acid, methanol, ethanol, dioxane or the like can be exemplified. The reduction reaction condition can suitably be selected depend on the catalyst to be used, and generally the reaction can be carried out at $-50°$ to $100°$ C., and is completed within 0.5 to 10 hours. For example, in case of using stannous chloride with hydrochloric acid used as the reducing agent, the reaction can advantageously be carried out at about $-20°$ to $50°$ C. The amount of the reducing agent can be at least an equimolar quantity, generally an equimolar to 3 times the molar quantity to the starting material. In the above-mentioned reaction, the nitro group of compound of the general formula (24) is fist changed to amino group to form a compound represented by the general formula (24'):

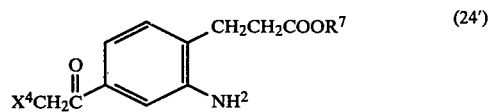

wherein $R^7$ and $X^4$ are the same as defined previously. Then this compound (24') is converted into a carbostyril compound (25) by ring closing reaction. In the reaction of reducing a compound (24) to a compound (24'), the carbonyl group in the compound (24) is not affected under the condition of reduction (2), however under the condition of reduction (1), the carbonyl group is sometimes converted into methylene group. By selecting the reducing conditions suitably, the carbonyl group can be kept as it is. The reaction of a compound of the general formula (25) with a compound of the general formula (12) can be carried out by a procedure similar to that described in the reaction of a compound of the general formula (1-d) with a compound of the general formula (12) as mentioned previously.

REACTION PROCESS FORMULA-10b

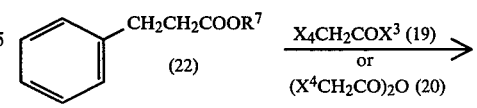

-continued

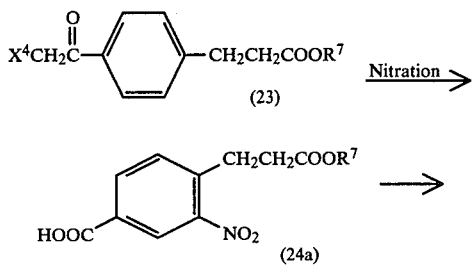

wherein $R^7$, $X^3$ and $X^4$ are the same as defined previously.

The nitration of a compound (23) can be carried out under conditions similar to the nitration of a compound (23) in reaction process formula-10a, except the reaction temperature which may suitably be selected. The reaction can advantageously be carried out at a temperature within $-10°$ C. to a room temperature.

The reaction for obtaining a compound of the general formula (2a) by reducing and ring closing a compound of the general formula (24a) can be carried out under conditions similar to the reaction for obtaining a compound of the general formula (26) as described in reaction process formula-10a. In the above-mentioned reaction, the nitro group of a compound (24a) is first changed to an amino group to form a compound of the general formula (24a'),

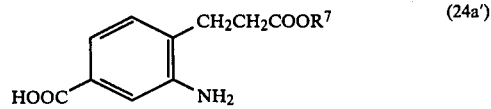

wherein $R^7$ is the same as defined previously.

A compound of the general formula (24a') is then converted into a carbostyril compound of the general formula (2a) by ring closing reaction.

REACTION PROCESS FORMULA-11

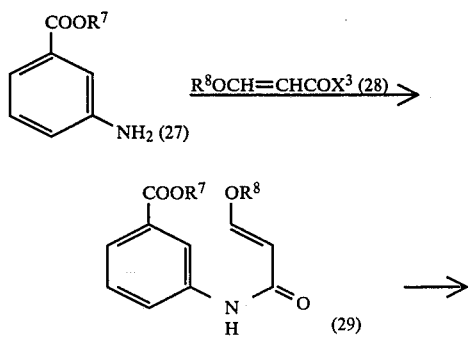

-continued

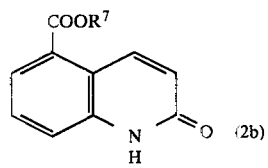

wherein $R^7$ and $X^3$ are the same as defined above; $R^8$ is a lower alkyl group.

The reaction of a compound of the general formula (27) with a compound of the general formula (28) can be carried out under conditions similar to the reaction of a compound (4) with a compound (5), wherein the compound (5) is a carboxylic acid halide, except the ratio of the amounts of the reactants. The reaction can be carried out even in the absence of a basic compound, and the ratio of the amount of a compound of the general formula (27) to the amount of a compound of the general formula (28) may be at least in an equimolar quantity, preferably 1 to 5 times the molar quantity to the latter. The cyclization reaction of a compound of the general formula (29) can be carried out in the presence of an acid in the absence or presence of a suitable solvent. As to the acid to be used is not specifically restricted and any inorganic acid or organic acid can be used, concretely, an inorganic acid such as hydrochloric acid, hydrobromic acid, sulfuric acid, a Lewis acid such as aluminium chloride, boron trifluoride, titanium tetrachloride or the like, an organic acid such as formic acid, acetic acid, ethanesulfonic acid, p-toluenesulfonic acid can be exemplified. Among these acids, hydrochloric acid, hydrobromic acid, sulfuric acid are specifically preferable. The amount of the acid to be used is not specifically restricted, the amount can be selected from a wide range, generally at least an equivalent weight, preferably 10 to 50 parts by weight of the acid may be used to the weight of a compound of the general formula (29). As to the solvent, any inert solvent can be used, for example, water, a lower alcohol such as methanol, ethanol, propanol or the like, an ether such as dioxane, tetrahydrofuran or the like, an aromatic hydrocarbon such as benzene, toluene or the like, a halogenerated hydrocarbon such as methylene chloride, chloroform, carbon tetrachloride or the like, acetone, dimethyl sulfoxide, dimethylformamide, hexamethylphosphoric triamide or the like can be exemplified. Among these solvents, a water-soluble solvent such as a lower alcohol, an ether, acetone, dimethyl sulfoxide, dimethylformamide, hexamethylphosphoric triamide or the like are preferable. This reaction is carried out generally at 0° to 100° C., preferably at room temperature to 60° C., and the reaction is generally completed in 5 minutes to 6 hours.

REACTION PROCESS FORMULA-12

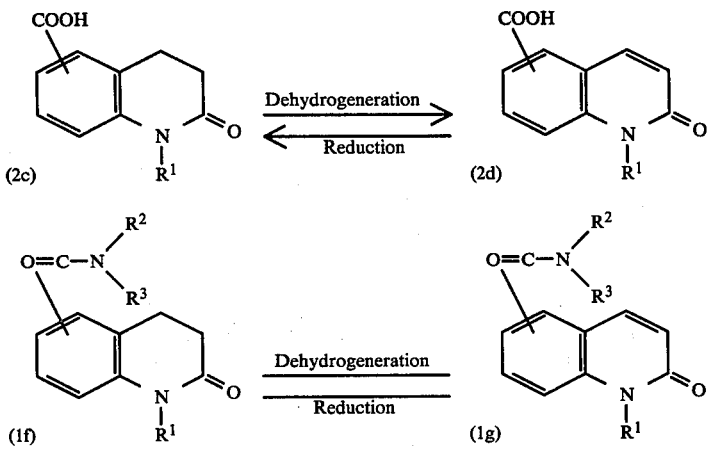

wherein $R^1$, $R^2$ and $R^3$ are the same as defined previously.

The reduction of a compound of the general formula (1g) or (2d) can be carried out by applying a condition of usual catalytic reduction. As to the catalyst used in this reduction, a metal catalyst such as palladium, palladium-carbon, platinum, Raney nickel or the like can be exemplified. Said metal catalyst may be used in an usual catalytic amount. As to the solvent, water, methanol, ethanol, isopropanol, dioxane, tetrahydrofuran, hexane, cyclohexane, ethyl acetate or the like can be exemplified or a mixture of the exemplified solvents can also be used. The reduction can be carried out at a normal pressure or under a pressurized condition, generally the reduction may be carried out at a normal pressure to 20 kg/cm$^2$, preferably at a normal pressure to 10 kg/cm$^2$. The reduction may be carried out generally at 0° to 150° C., preferably at a room temperature to 100° C.

The dehydrogeneration of a compound of the general formula (1f) or (2c) can be carried out in a suitable solvent. As to the oxidizing agent to be used in this reaction, a benzoquinone such as 2,3-dichloro-5,6-dicyanobenzoquinone, chloranil (2,3,5,6-tetrachlorobenzoquinone) or the like, a halogenating agent such as N-bromosuccinimide, N-chlorosuccinimide or the like, a dehydrogenating catalyst such as selenium dioxide, palladium-carbon, palladium black, palladium oxide, Raney nickel or the like can be exemplified. There is not any specific restriction to the amount of the oxidizing agent and the amount can be selected from a wide range, generally an equimolar quantity to 5 times the molar quantity, preferably 1 to 2 times the moar quantity of the oxidizing agent can be used to the compound of the general formula (1f) or (2c). In case of using the dehydrogenating catalyst, generally an usual excess amount may be used. As to the solvent to be used in this reaction, an ether such as dioxane, tetrahydrofuran, methoxyethanol, dimethoxyethane or the like, an aromatic hydrocarbon such as benzene, toluene, xylene, cummene or the like, a halogenated hydrocarbon such as dichloromethane, dichloroethane, chloroform, carbon tetrachloride or the like, an alcohol such as butanol, amylalcohol, hexanol or the like, a protic polar solvent such as acetic acid or the like an aprotic polar solvent such as dimethylformamide, dimethyl sulfoxide, hexamethylphosphoric trimamide or the like can be exemplified. The reaction can be carried out at a room temperature to 300° C., preferably a room temperature to 200° C. and the reaction is generally completed in 1 to 40 hours.

Among the compounds represented by the general formula (1) of the present invention, those having hydrogen atom for the symbol $R^1$ further having double bond in the carbon-carbon bond between 3- and 4-positions in the carbostyril skeleton capable of existing in tautomeric system in the form of lactim-lactam as shown in the following reaction process formula-13.

REACTION PROCESS FORMULA-13

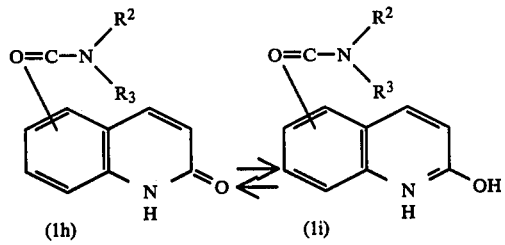

Among the compounds represented by the general formula (1) of the present invention, compounds having basic group can easily be converted into their acid addition salts by reacting with pharmaceutically acceptable acids. The examples of such acids including inorganic acids such as hydrochloric acid, sulfuric acid, phosphoric acid, hydrobromic acid or the like; organic acids such as oxalic acid, maleic acid, fumaric acid, malic acid, tartaric acid, citric acid, benzoic acid or the like.

The desired compounds as prepared by the procedures in the above-mentioned various reaction process formulas can easily be isolated and purified by usual separation means such as solvent extraction, dilution, recrystallization, column chromatography, preparative thin-layer chromatography.

Carbostyril derivatives of the present invetion also including their optical isomers.

Carbostyril derivatives of the general formula (1) can be used in the form of pharmaceutical composition together with usual pharmaceutically acceptable carriers. The examples of the carriers which are used depending on the desired form of pharmaceutical composition, including diluents or excipients such as fillers, diluents, binders, wetting agents, disintegrators, surface active agents, lubricants.

No particular restriction is made to the administration unit forms and the compositions can be selected in any desired unit form, including tablets, pills, powders, liquors, suspensions, emulsions, granules, capsules, suppositories, injections (solutions and suspensions) and ointments.

For the purpose of to shape in the form of tablets, carriers which are known in this field can also be used, for example excipients such as lactose, sucrose, sodium chloride, glucose, ures, starch, calcium carbonate, caolin, crystalline cellulose, silici acid; binding agents such as water, ethanol, propanol, simple syrup, solution of glucose, starch solution, gelatin solution, carboxymethylcellulose, shelac, methylcellulose, calcium phosphate and polyvinylpyrrolidone; desintegrators such as dried starch, sodium alginate, agar-agar powder, laminalia powder, sodium hydrogencarbonate, calcium carbonate, Tweens, sodium laurylsulfate, monoglyceride of stearic acid, starch, lactose; desintegration inhibitors such as sucrose, stearin, coconut butter, hydrogenated oil; adsorption accelerators such as quarternary ammonium base, sodium laurylsulfate; wetting agents such as glycerin, starch; adsorbing agents such as starch, lactose, caoline, bentonite, colloidal silicic acid; lubricants such as purified talc, stearic acid salt, boric acid powder, polyethylene glycol. In case of preparing tablets, they can be further coated with the usual coating materials to make sugar coated tablets, gelatin film coated tablets, tablets coated with enteric coatings, tablets coated with films or double layered tablets and multilayered tablets.

For the purpose of to shape in the form of pills, carriers which is known and widely used in this field can also be used, for example, excipients such as glucose, lactose, starch, coconut butter, hydrogenated oils, caolin and talc; binders such as powdered gumi ababicum, powdered Tragacanth, gelatin and ethanol; desintegrators such as laminaria and agar-agar are included.

For the purpose of to shape in the form of suppositories, carriers which are known and widely used in this field can also be used, for example, polyethylene glycols, coconut butter, higher alcohols, esters of higher alcohols, gelatin and semi-synthesized glycerides are included.

For the purpose of to make in the form of injection preparations, solutions and suspensions are sterilized and are preferably isotonic to blood. In making injection preparations, every carriers which are commonly used in this field can also be used, for example, water, ethyl, alcohol, propylene glycol, ethoxylated isostearyl alcohol, polyxylated isostearyl alcohol, polyoxyethylene sorbitol, sorbitane esters are included. In these instances, adequate amounts of sodium chloride, glucose or glycerin can be added to contain in the desired preparations for the purpose of to have them isotonic. Furthermore, the usual dissolving agents, buffers, analgesic agents, preservitives can be added as well as coloring materials, perfumes, seasoning agents, sweetening agents and other medicines can also be added into the desired preparations, if necessary.

The amount of a compound of the general formula (1) to be contained in the pharmaceutical preparation (cardiotonic composition) is not specifically restricted and it can suitably be selected from a wide range, and usually 1 to 70% by weight, preferably 1 to 30% by weight of the whole composition is preferable.

The above-mentioned cardiotonic composition can be used in various forms depending on the purpose without any restriction, thus the composition is administered in a suitable method according to the forms of the preparation, the age of the patient, the distinction of sex, the condition of the symptoms and other factors. For example, tablets, pills, solutions, suspensions, emulsions, granules and capsuled are administered orally; and injection preparations are administered intravenously singly or are mixed with injection transfusions such as glucose solutions and amino acids solution; if necessary the injection preparations are administered singly intramuscularly, intracutaneously, subcutaneously or intraperitoneally; suppositories are administered into rectum.

The dosage of the present cardiotonic composition is suitably selected according to the usage, the age of the patient, the distinction of sex, the condition of the symptoms and other factors, generally 0.01 to 10 mg/kg of body weight/day of a compound of the general formula (1) as the active ingredient may be administered, and 0.1 to 200 mg of the active ingredient may be contained in the administration unit form.

Examples of cardiotonic composition containing carbostyril derivative of the present invention are shown as follows:

EXAMPLE OF PREPARATION OF TABLETS-1

By using an usual procedure, tablets having the following formulation were prepared.

| | |
|---|---|
| 6-[4-(3,4-Dimethoxybenzyl)-1-piperazinylcarbonyl]-3,4-dihydrocarbostyril | 5 mg |
| Starch | 132 mg |
| Magnesium stearate | 18 mg |
| Lactose | 45 mg |
| Total | 200 mg |

EXAMPLE OF PREPARATION OF TABLETS-2

By suing an usual procedure, tablets having the following formulation were prepared.

| | |
|---|---|
| 6-[4-(2-Phenoxyethyl)-1-piperazinylcarbonyl]-3,4-dihydrocarbostyril | 10 mg |
| Starch | 127 mg |
| Magnesium stearate | 18 mg |
| Lactose | 45 mg |
| Total | 200 mg |

EXAMPLE OF PREPARATION OF TABLETS-3

By using an usual procedure, tablets having the following formulation were prepared.

| | |
|---|---|
| 6-(4-Isobutyryl-1-piperazinyl-carbonyl)-3,4-dihydrocarbostyril monohydrochloride | 5 mg |
| Starch | 132 mg |
| Magnesium stearate | 18 mg |
| Lactose | 45 mg |
| Total | 200 mg |

EXAMPLE OF PREPARATION OF INJECTIONS

| | |
|---|---|
| 6-(4-Benzyl-1-piperazinyl-carbonyl)-3,4-dihydrocarbostyril | 500 mg |
| Polyethylene glycol | |

| | | |
|---|---|---|
| (Molecular weight: 4,000) | 0.3 | g |
| Sodium chloride | 0.9 | g |
| Polyoxyethylene sorbitan monooleate | 0.4 | g |
| Sodium metabisulfite | 0.1 | g |
| Methyl p-hydroxybenzoate | 0.18 | g |
| Propyl p-hydroxybenzoate | 0.02 | g |
| Distilled water for injection | 100 | ml |

Above prescribed methyl p-hydroxybenzoate, propyl p-hydroxybenzoate, sodium chloride and sodium metabisulfite were dissolved in about a half the quantity of distilled water at 80° C. under stirring. The obtained solution is cooled to 40° C., and 6-(4-benzyl-1-piperazinylcarbonyl)-3,4-dihydrocarbostyril, polyethylene glycol and polyoxyethylene sorbitan monooleate are dissolved in that order in said solution. This solution was further added with distilled water for injection to the final regulated volume and then sterilized by sterile filtration with a suitable filter page. One milliliter each of the obtained solution was filled in an ampoule separately to make injection preparations.

Pharmacological activities of compounds of the general formula (1) of the present invention were conducted by test methods as explained below with the following results.

Compounds used in the tests are as follows:

| Compound No. | Name of the compound |
|---|---|
| 1 | 6-(1-Piperazinylcarbonyl)-3,4-dihydrocarbostyril |
| 2 | 6-[4-(2-Phenoxyethyl)-1-piperazinylcarbonyl]-3,4-dihydrocarbostyril |
| 3 | 6-[4-(2-Cyanoethyl)-1-piperazinylcarbonyl]-3,4-dihydrocarbostyril monohydrochloride |
| 4 | 6-(4-Methyl-1-piperazinylcarbonyl)-3,4-dihydrocarbostyril |
| 5 | 6-[4-(3,4-Dimethoxybenzoyl)-1-piperazinylcarbonyl]-3,4-dihydrocarbostyril |
| 6 | 6-[4-(4-Cyanobenzoyl)-1-piperazinylcarbonyl]-3,4-dihydrocarbostyril |
| 7 | 6-[4-(4-Methoxybenzoyl)-1-piperazinylcarbonyl-3,4-dihydrocarbostyril |
| 8 | 6-[4-(3-Chlorobenzoyl)-1-piperazinylcarbonyl]-3,4-dihydrocarbostyril |
| 9 | 6-[4-(3,4-Dichlorobenzoyl)-1-piperazinylcarbonyl]-3,4-dihydrocarbostyril |
| 10 | 6-[4-(4-Nitrobenzoyl)-1-piperazinylcarbonyl]-3,4-dihydrocarbostyril |
| 11 | 6-[4-(4-Methylbenzoyl)-1-piperazinylcarbonyl]-3,4-dihydrocarbostyril |
| 12 | 6-(4-Ethoxycarbonyl-1-piperazinylcarbonyl)-3,4-dihydrocarbostyril |
| 13 | 6-(4-Furoyl-1-piperazinylcarbonyl)-3,4-dihydrocarbostyril |
| 14 | 6-(4-Benzyl-1-piperazinylcarbonyl)-3,4-dihydrocarbostyril monohydrochloride |
| 15 | 6-[4-(4-Methylbenzyl)-1-piperazinylcarbonyl]-3,4-dihydrocarbostyril |
| 16 | 6-[4-(4-Methoxybenzyl)-1-piperazinylcarbonyl]-3,4-dihydrocarbostril monohydrochloride |
| 17 | 6-[4-(4-Chlorobenzyl)-1-piperazinylcarbonyl]-3,4-dihydrocarbostyril monohydrochloride |
| 18 | 6-[4-(3,4-Dimethoxybenzyl)-1-piperazinylcarbonyl]-3,4-dihydrocarbostyril monohydrochloride |
| 19 | 6-[4-(4-Nitrobenzyl)-1-piperazinylcarbonyl-3,4-dihydrocarbostyril monohydrochloride |
| 20 | 6-[N—Methyl-N—(4-methoxybenzyl)carbamoyl]-3,4-dihydrocarbostyril |
| 21 | 6-[N—Methyl-N—(3,4-methylenedioxybenzyl)-carbamoyl]-3,4-dihydrocarbostyril |
| 22 | 6-[N—Methyl-N—(4-chlorobenzyl)carbamoyl]-3,4-dihydrocarbostyril |
| 23 | Amrinone: [3-Amino-5-(4-pyridinyl-)-2-(H)—pyridinone] |
| 24 | 6-[4-(2-Phenoxyethyl)-1-piperazinylcarbonyl]-carbostyril monohydrochloride |
| 25 | 6-[4-(3-Phenylpropyl)-1-piperazinylcarbonyl]-carbostyril monohydrochloride |
| 26 | 6-[4-(2-Benzoylethyl)-1-piperazinylcarbonyl]-3,4-dihydrocarbostyril |
| 27 | Dobutamine: 3,4-Dihydroxy-N—[3-(4-hydroxyphenyl)-1-methylpropyl]-β-phenylethylamine |
| 28 | 6-[4-(4-Chlorobenzyl)-1-piperazinylcarbonyl]-carbostyril monohydrochloride |
| 29 | 6-[4-(3-Benzoylpropyl)-1-piperazinylcarbonyl]-3,4-dihydrocarbostyril monohydrochloride ½-hydrate |
| 30 | 6-[4-(4-Hydroxybenzoyl)methyl-1-piperazinylcarbonyl]-3,4-dihydrocarbostyril monohydrochloride ½-hydrate |
| 31 | 6-(4-Propyl-1-piperazinylcarbonyl)-3,4-dihydrocarbostyril |
| 32 | 6-[4-(3-Chlorobenzoyl)methyl-1-piperazinylcarbonyl]-3,4-dihydrocarbostyril monohydrochloride ½-hydrate |
| 33 | 6-(4-Isopentyl-1-piperazinylcarbonyl)-3,4-dihydrocarbostyril |
| 34 | 6-[4-(4-Methylthiobenzyl)-1-piperazinylcarbonyl]-3,4-dihydrocarbostyril monohydrochloride |
| 35 | 6-[4-(3,4,5-Trimethoxybenzyl)-1-piperazinylcarbonyl]-3,4-dihydrocarbostyril monohydrochloride |
| 36 | 6-[4-(4-Aminobenzyl)-1-piperazinylcarbonyl]-3,4-dihydrocarbostyril |
| 37 | 6-[4-(4-Acetylaminobenzyl)-1-piperazinylcarbonyl]-3,4-dihydrocarbostyril monohydrochloride 3/2-hydrate |
| 38 | 6-(4-Isobutyl-1-piperazinylcarbonyl)carbostyril monohydrochloride ½-hydrate |
| 39 | 6-[4-(4-Methylbenzoylmethyl)-1-piperazinylcarbonyl]-3,4-dihydrocarbostyril monohydrochloride |
| 40 | 6-(4-Cyclohexylmethyl-1-piperazinylcarbonyl)-3,4-dihydrocarbostyril monohydrochloride |
| 41 | 6-(4-Isobutyl-1-piperazinylcarbonyl)-3,4-dihydrocarbostyril monohydrochloride |
| 42 | 6-(4-Propargyl-1-piperazinylcarbonyl)-3,4-dihydrocarbostyril monohydrochloride |
| 43 | 6-[4-(4-Methoxybenzoyl)methyl-1-piperazinylcarbonyl]-3,4-dihydrocarbostyril monohydrochloride |
| 44 | 6-(4-n-Hexyl-1-piperazinylcarbonyl)-3,4-dihydrocarbostyril monohydrochloride |
| 45 | 1-Methyl-6-(4-benzyl-1-piperazinylcarbonyl)-3,4-dihydrocarbostyril |
| 46 | 6-(4-Allyl-1-piperazinylcarbonyl)-3,4-dihydrocarbostyril monohydrochloride |
| 47 | 1-Propargyl-6-[4-(2-phenoxyethyl)-1-piperazinylcarbonyl]-3,4-dihydrocarbostyril monohydrochloride |
| 48 | 1-Benzyl-6-[4-(2-phenoxyethyl)-1-piperazinylcarbonyl]-3,4-dihydrocarbostyril monohydrochloride |
| 49 | 1-Allyl-6-[4-(2-phenoxyethyl)-1-piperazinylcarbonyl]-3,4-dihydrocarbostyril monohydrochloride |
| 50 | 6-[4-(2-Hydroxyethyl)-1-piperazinylcarbonyl]-3,4-dihydrocarbostyril dihydrate |
| 51 | 6-(1-Piperidylcarbonyl)-3,4-dihydrocarbostyril |
| 52 | 6-(4-Methyl-1-piperidylcarbonyl)-3,4-dihydrocarbostyril |
| 53 | 6-(4-Benzyl-1-piperidylcarbonyl)-3,4-dihydrocarbostyril ½-hydrate |
| 54 | 6-(1-Pyrrolidylcarbonyl)-3,4-dihydrocarbostyril |
| 55 | 6-{4-[3-(2-Chlorophenoxy)propyl]-1-piperazinylcarbonyl}-3,4-dihydrocarbostyril monohydrochloride |
| 56 | 6-{4-[2-(4-Methoxyphenoxy)ethyl]-1-piperazinylcarbonyl}-3,4-dihydrocarbostyril monohydrochloride |
| 57 | 6-{4-[2-(3,4-Methylenedioxyphenoxy)ethyl]-1-piperzinylcarbonyl}-3,4-dihydrocarbostyril monohydrochloride |
| 58 | 6-[4-(5-Benzoylpentyl)-1-piperazinylcarbonyl]- |

-continued

Compounds used in the tests are as follows:

| Compound No. | Name of the compound |
|---|---|
| | 3,4-dihydrocarbostyril monohydrochloride monohydrate |
| 59 | 6-{4-[3-(3,4-Dimethoxybenzoyl)propyl]-1-piperazinylcarbonyl}-3,4-dihydrocarbostyril monohydrochloride ½-hydrate |
| 60 | 6-[4-(3-Chlorocinnamoyl)-piperazinylcarbonyl]-3,4-dihydrocarbostyril ¼-hydrate |
| 61 | 6-[4-(3,4,5-Trimethoxycinnamoyl)-1-piperazinylcarbonyl]-3,4-dihydrocarbostyril |
| 62 | 6-[4-(2-Acetyloxypropyl)-1-piperazinylcarbonyl]-3,4-dihydrocarbostyril monohydrochloride ½-hydrate |
| 63 | 5-(4-Isobutyl-1-piperazinylcarbonyl)carbostyril monohydrochloride ½-hydrate |
| 64 | 7-(4-Benzyl-1-piperazinylcarbonyl)-3,4-dihydrocarbostyril monohydrochloride |
| 65 | 8-[4-(3-Phenylpropyl)-1-piperazinylcarbonyl]-3,4-dihydrocarbostyril monohydrochloride |
| 66 | 6-(4-Ethoxycarbonylmethyl-1-piperazinylcarbonyl)-3,4-dihydrocarbostyril monohydrochloride |
| 67 | 6-[4-(2-Ethoxycarbonylethyl)-1-piperazinylcarbonyl]-3,4-dihydrocarbostyril |
| 68 | 6-[4-(2-Chloropropyl)-1-piperazinylcarbonyl]-3,4-dihydrocarbostyril monohydrochloride |
| 69 | 6-(4-Methanesulfonyl-1-piperazinylcarbonyl)-3,4-dihydrocarbostyril |
| 70 | 6-(4-Formyl-1-piperazinylcarbonyl)-3,4-dihydrocarbostyril |
| 71 | 6-{4-[2-(4-Acetylaminobenzoyl)ethyl]-1-piperazinylcarbonyl}-3,4-dihydrocarbostyril |
| 72 | 6-[4-(4-Methoxyphenylacetyl)-1-piperazinylcarbonyl]-3,4-dihydrocarbostyril |

PHARMACOLOGICAL TEST-1

Adult mongrel dogs of either sex, weighing 8–13 kg, were anesthetized with sodium pentobarbital at a rate of 30 mg/kg by intraveneous administration. After another intraveneous administration of sodium heparin at a rate of 1,000 U/kg, the test dog was sacrifieced by blood letting. The heart of the dog was excised and immediately plunged into Locke's solution, then the right coronary artery was cannulated to the atrionector artery and the right atrium was carefully isolated.

Next, the donor adult mongrel dogs of either sex, weighing 18–27 kg, were anesthetized with sodium pentobarbital at a rate of 30 mg/kg by intraveneous administration, and further treated with intraveneous administration of sodium heparin at a rate of 1,000 U/kg.

The above-mentioned right atrium was perfused with the blood conducted from the carotid artery of the donor dog by aid of Peristaric pump. The perfusion pressure was maintained at 100 mm-Hg constantly. The movement of the right atrium was measured through a force-displacement transducer under a static tension of 2 g. The amount of blood flown in the coronary arteries was measured by electromagnetic flow meter. All the data were recorded on an ink-writing recorder. [The method of this test is reported in an article written by Chiba et al., "Japan Journal of Pharmacology, 25, 433–439, (1975), Naunyn-Schmiedberg's Arch. Pharmacology, 289, 315–325, (1975).]

A solution containing a compound to be tested was injected into the artery through the rubber tube connected close to the cannula, in an amount of 10–30 ul.

Positive inotropic effect of the compound to be tested is expressed as a percentage of the developed tension before and after the injection of the compound. The effect of the compound on blood flow in coronary artery is expressed as an absolute value (ml/minute) measured from before the injection of the compound.

The results are shown in Tables 1 and 2 below.

TABLE 1

| Compound No. | Dosage | Change of atrial muscle contriction | Change of blood flow in coronary artery |
|---|---|---|---|
| 1 | 1 u mol | 11.7% | 1 ml/minute |
| 2 | 1 u mol | 165.0 | 4 |
| 3 | 300 n mol | 24.3 | — |
| 4 | 1 u mol | 65.8 | 1.5 |
| 5 | 1 u mol | 63.2 | — |
| 6 | 300 n mol | — | 1 |
| 7 | 300 n mol | 21.4 | — |
| 8 | 300 n mol | 20.5 | — |
| 9 | 300 n mol | 24 | — |
| 10 | 100 n mol | 10.5 | — |
| 11 | 300 n mol | 23.2 | 2 |
| 12 | 1 u mol | 125.0 | 2.5 |
| 13 | 1 u mol | 80.0 | 1 |
| 14 | 1 u mol | 145.5 | 1.5 |
| 15 | 1 u mol | 96.2 | 1.5 |
| 16 | 1 u mol | 132.0 | 2.5 |
| 17 | 1 u mol | 68.0 | 2 |
| 18 | 1 u mol | 114.6 | 3 |
| 19 | 1 u mol | 94.6 | 1.5 |
| 23(a) | 1 u mol | 57.5 | — |

TABLE 2

| Compound No. | Dosage | Change of atrial muscle contriction | Change of blood flow in coronary artery |
|---|---|---|---|
| 20 | 300 n mol | 42.2% | 2.0 ml/minute |
| 21 | 300 n mol | 42.0 | 1.5 |
| 22 | 300 n mol | 53.5 | 1.5 |
| 23(b) | 1 u mol | 58.8 | — |

PHARMACOLOGICAL TEST-2

Mongrel dogs of either sex, weighing 9–15 kg, were anesthetized with sodium pentobarbital initially in a dosage of 30 mg/kg intravenously and subsequently at a rate of 4 mg/kg/hr intravenously by using an infusion pump. The animals were respired with room air in a tidal volume of 20 ml/kg at a rate of 18 beats/minute by using respirator. The chest was opened by a midline incision and the heart was suspended in the pericardial cradle.

The contractile force of the myocardium was measured by means of a Walton-Brodie type strain-gauge arch sutured onto the left ventricle. Systemic blood pressure was measured from the left femoral artery by a pressure transducer. All recordings were made on a chart by the use of a rectilinear recorder.

A compound to be tested was injected into the left femoral vein.

The inotropic effects of the compounds are expressed as a percentage of the developed tension before the injection on the compound.

The effect of the compound on blood pressure (mm-Hg) is expressed as a difference between the values before and after the injection of the compound.

The results are shown in Table 3 below.

TABLE 3

| Compound No. | Dosage (mg/kg) | Change of contriction of left venticle (%) | Blood pressure (mm-Hg) | |
|---|---|---|---|---|
| | | | Diostasis | Systole |
| 24 | 1 | 74.4 | −52 | −34 |

TABLE 3-continued

| Compound No. | Dosage (mg/kg) | Change of contriction of left venticle (%) | Blood pressure (mm-Hg) | |
|---|---|---|---|---|
| | | | Diostasis | Systole |
| 25 | 1 | 29.6 | −42 | −24 |
| 26 | 1 | 17.9 | −20 | −18 |
| 14 | 1 | 40.5 | −36 | −22 |
| 2 | 1 | 20.0 | −38 | −44 |
| 27 | 0.01 | 83.9 | −30 | 32 |

PHARMACOLOGICAL TEST-3

Adult mongrel dogs of either sex, weighing 8–13 kg, were anesthetized with sodium pentobarbital at a rate of 30 mg/kg by intraveneous administration. After another intraveneous administration of sodium heparin at a rate of 1,000 U/kg, the test dog was sacrificed by blood letting. The heart of the dog was excised and the preparation was essentially consisting from the anterior papillary muscle excised together with the ventricular septum and was set up in cold Tyrode's solution. The preparation was placed in a glass water jacket maintained at about 38° C. and cross-circulated through the cannulated anterior septal artery with blood from a donor dog at a constant pressure of 100 mm-Hg. The dogs used as donors were weighing 18–27 kg, and were anesthetized with pentobarbital sodium at a rate of 30 mg/kg by intraveneous administration, and further treated with intraveneous administration of sodium heparin at a rate of 1,000 U/kg. The papillary muscle was driven with rectangular pulse about 1.5 times the threshold voltage (0.5–3 volts) and 5 seconds duration at a fixed rate of 120 beats/minute through bipolar pacing electrodes. Tension developed by the papillary muscle was measured by a strain-gauge transducer. The muscle was loaded with a weight of about 1.5 g. Blood flow through the anterior septal artery was measured by an electromagnetic flow meter. Recording of developed tension and blood flow was made on charts with an ink-writing rectigraph. [The details of this test method is reported in an article written by Endoh and Hashimoto, "American Journal of Physiology, 218, 1459–1463, (1970)".]

A compound to be tested was injected into the intra-arterially in an amount of 10–30 ul in 4 seconds.

The inotropic effects of the compounds are expressed as a percentage of the developed tension before the injection of the compound.

The effect of the compound of blood flow are expressed as a difference (ml/minute) of the values before and after the injection of the compound.

The results are shown in Table 4 below.

TABLE 4

| Compound No. | Dosage | Change of arterial muscle contriction | Change of blood flow in coronary artery |
|---|---|---|---|
| 50 | 1 u mol | 8.0% | 0.5 ml/minute |
| 51 | 1 u mol | 25.6 | 1.5 |
| 52 | 1 u mol | 39.5 | 2.5 |
| 53 | 300 n mol | 10.4 | 1.0 |
| 54 | 1 u mol | 28.6 | 0.5 |
| 55 | 1 u mol | 46.8 | 1.5 |
| 56 | 1 u mol | 13.5 | 4 |
| 57 | 1 u mol | 13.2 | 3.5 |
| 58 | 1 u mol | 45.5 | 3.8 |
| 59 | 1 u mol | 25.0 | 1.5 |
| 60 | 300 n mol | 12.5 | 1.0 |
| 61 | 1 u mol | 48.0 | — |
| 62 | 1 u mol | 8.3 | 3.5 |
| 63 | 3 u mol | 10 | — |
| 64 | 1 u mol | 9.0 | 1.9 |
| 65 | 1 u mol | 6.6 | 0.9 |
| 66 | 1 u mol | 11.8 | 0.6 |
| 67 | 1 u mol | 25.0 | 1.2 |
| 68 | 1 u mol | 31.8 | 4.1 |
| 69 | 3 u mol | 10 | — |
| 70 | 3 u mol | 10 | — |
| 71 | 3 u mol | 19.4 | — |
| 72 | 1 u mol | 20.8 | 5.5 |
| 23(a) | 1 u mol | 54.8 | — |

The present invention will be illustrated more in specifically by way of following examples, in which the preparation of the compounds to be used as the starting materials will be shown in Reference Examples and the preparation of the objective compounds will be shown in Examples.

REFERENCE EXAMPLE 1

50 Grams of 6-(α-pyridiniumacetyl)-3,4-dihydrocarbostyril chloride and 50 g of sodium hydroxide were suspended in 1 liter of water and the suspension was stirred at 90° to 100° C. for 3 hours. After the reaction was completed, a certain amount of concentrated hydrochloric acid was added to the reaction mixture so as to make the pH value of the mixture to about pH 2 to precipitate crystals, then the crystals were collected by filtration. Recrystallization from dimethylformamide to obtain 19.1 g of 6-carboxy-3,4-dihydrocarbostyril. Melting point: over 300° C. Light yellow powdery crystals.

REFERENCE EXAMPLE 2

10 Grams of 6-carboxy-3,4-dihydrocarbostyril and 6.0 g of N-hydroxysuccinimide were suspended in 200 ml of dioxane. Then a solution of 12.4 g of dichlorohexylcarbodiimide in 50 ml of dioxane was added dropwise of the suspension under ice-cooling with stirring. The reaction mixture was heated at 90° C. for 4 hours. After the reaction was completed, the reaction mixture was cooled to a room temperature, and the crystals being precipitated were removed by filtration and the mother liquor was concentrated by distillation. The residue was recrystallized from dimethylformamide-ethanol to obtain 10.8 g of succinimide 3,4-dihydrocarbostyril-6-carboxylate. Melting point: 234.5°–236° C. Colorless flake-like crystals.

REFERENCE EXAMPLE 3

15.1 Grams of 6-acetyl-3,4-dihydrocarbostyril was disolved in 100 ml of acetic acid and the solution was kept at a temperature of 35°–40° C. 10 Milliliter of acetic acid containing 11.2 ml of bromine was added dropwise to the above-mentioned solution for 3.5 hours under stirring. The reaction mixture was allowed to stand over night and the crystals precipitated in the mixture were collected by filtration and washed with a small amount of acetic acid. The crystals thus obtained were treated with activated carbon by using ethanol as a solvent. Recrystallized from ethanol to obtain 19.5 g of 6-dibromoacetyl-3,4-dihydrocarbostyril in the form of light yellow needle-like crystals. Melting point: 168°–169° C.

REFERENCE EXAMPLE 4

Into 250 ml of water, 26 g sodium hydroxide was dissolved, then at a temperature of 90°–100° C. and under stirring condition, 35 g of 6-dibromoacetyl-3,4-dihydrocarbostyril was added thereinto and reacted for 3 hours. After the reaction was completed, the reaction mixture was cooled and insoluble matters formed in the mixture were removed by filtration. The mother liquor was acidified with concentrated hydrochloric acid and the crystals precipitated were collected by filtration and washed with water. The crystals thus obtained were recrystallized from ethanol twice to obtain 10.5 g of 6-carboxy-3,4-dihydrocarbostyril in the form of light yellow amorphous crystals. Melting point: 324.5°–327° C. (decomposed).

REFERENCE EXAMPLE 5

60 Grams of 6-($\alpha$-chloroacetyl)carbostyril was suspended in 0.5 kg of pyridine and stirred at 80°–90° C. for 2 hours, then the suspension was stirred under ice-cooling for 1 hour. The crystals thus precipitated were collected by filtration and recrystallized from methanol to obtain 70 g of 6-($\alpha$-pyridiniumacetyl)carbostyril chloride $\frac{1}{2}$-hydrate in the form of colorless needle-like crystals. Melting point: over 300° C.

REFERENCE EXAMPLE 6

69.7 Grams of 6-($\alpha$-pyridiniumacetyl)carbostyril chloride and 65 g of sodium hydroxide were dissolved in 0.6 liter of water and stirred at a temperature of 60°–70° C. for 3 hours. Under the ice-cooled condition, to the reaction mixture was added concentrated hydrochloric acid so as to adjust the pH of the reaction mixture to about pH 2. Precipitated crystals were collected by filtration and recrystallized from dimethylformamide to obtain 41.4 g of 6-carboxycarbostyril. Light brown powdery crystals. Melting point: over 300° C.

REFERENCE EXAMPLE 7

100 Grams of m-aminobenzoic acid was suspended in 1 liter of diethyl ether, and at a room temperature with stirring 44.6 g of $\beta$-ethoxyacrylic chloride was added dropwise. Then the reaction mixture was heated at 40° C. for 5 hours. After the reaction was completed, the precipitated matter was collected by filtration and washed with water three times, and dried, and recrystallized from methanol to obtain 60 g of m-carboxy-N-($\beta$-ethoxyacryloyl)aniline. Colorless cotton-like crystals. Melting point: 200.5°–202° C.

REFERENCE EXAMPLE 8

8 Grams of m-carboxy-N-($\beta$-ethoxyacryloyl)aniline was added in 80 ml of concentrated sulfuric acid and stirred at a room temperature for 2 hours, then stirred at 50° C. for 1 hour. The reaction mixture was poured into ice and the pH of the mixture was adjusted to pH 3–4 by adding 10N-sodium hydroxide aqueous solution. The precipitated crystals were collected by filtration and washed with water, recrystallized from dimethylformamide to obtain 4.26 g of 5-carboxycarbostyril. Light yellow powdery crystals. Melting point: over 320° C.

NMR (DMSO): $\delta$ 6.58 (d, J=9.5 Hz, 1H), 7.40–7.80 (m, 3H), 8.69 (d, J=9.5 Hz, 1H).

REFERENCE EXAMPLE 9

A mixture of 50 g of methyl 3-phenylpropionate, 51.6 g of chloroacetyl chloride and 250 ml of dichloromethane was cooled to 0° C. Then at 0° to 10° C. with stirring, 122 g of aluminum chloride was added slowly, stirred at a room temperature for 2 hours and allowed to stand overnight. The reaction mixture was poured into an ice-concentrated hydrochloric acid and extracted with chloroform, then the chloroform layer was washed with water, dried and the chloroform was removed by distillation to obtain the residue, then isopropyl ether was added to the residue to effect crystallization. The crystals were collected by filtration, and recrystallized from ethanol to obtain 53.4 g of methyl 3-(4-chloroacetylphenyl)-propionate. Colorless needle-like crystals. Melting point: 90°–92° C.

REFERENCE EXAMPLE 10

36.26 Grams of methyl 3-(4-chloroacetylphenyl)-propionate was dissolved in 300 ml of concentrated sulfuric acid, then 20.9 g of fuming nitric acid (d=1.52) was added dropwise under ice-cooled condition with stirring. The reaction mixture was stirred at a room temperature for 3 hours then the reaction mixture was poured into ice-water and extracted with chloroform. The chloroform layer was washed with water and dried, then chloroform was removed by distillation. The residue thus obtained was treated by a silica gel chromatography and crystallized by adding ether. The crystals were collected by filtration and recrystallized from methanol to obtain 26.7 g of methyl 3-(4-carboxyl-2-nitrophenyl)-propionate. Light yellow prism-like crystals. Melting point: 120°–122° C.

REFERENCE EXAMPLE 11

5 Grams of methyl 3-(4-carboxy-2-nitrophenyl)-propionate, 8.87 ml of 2.226N-sodium hydroxide methanol solution, 100 ml of methanol and 1 g of 5%-palladium-carbon (containing 50% of water) were mixed together and the mixture was catalytically reduced at a normal temperature and under a normal pressure. The catalyst was removed by filtration and to the mother liquor was added concentrated hydrochloric acid to adjust the pH to about 1 and the crystals formed were collected by filtration, recrystallized from methanol to obtain 3.62 g of 7-carboxyl-3,4-dihydrocarbostyril. Colorless needle-like crystals. Melting point: over 320° C.

NMR (DMSO): $\delta$=2.33–2.60 (m, 2H), 2.77–3.05 (m, 2H), 7.21 (d, J=8.5 Hz, 1H), 7.38–7.53 (m, 2H), 10.15 (s, 1H).

REFERENCE EXAMPLE 12

To a solution containing 467 g of chloroacetyl chloride in 400 ml of dichloromethane was added 735 g of aluminum chloride by way of one-third portion thereof in three times, at below 30° C., with stirring, then 200 g of the carbostyril was added to the mixture at the same temperature under stirring. Then the reaction mixture was refluxed for 6 hours. After the reaction was completed, the reaction mixture was poured into ice-concentrated hydrochloric acid and the crystals formed were collected by filtration, and washed with a hot methanol to obtain 153 g of 6-chloroacetylcarbostyril. The mother liquor was concentrated to dryness and the residue was purified by a silica gel column cromatography. Recrystallized from methanol to obtain 35.41 g of 8-chloroacetyl-carbostyril. Light yellow needle-like crystals. Melting point: 177.5°–179° C.

REFERENCE EXAMPLE 13

30 Grams of 8-chloroacetylcarbostyril was mixed with 300 ml of pyridine and stirred at 80°–90° C. for 2.5 hours under heating. Then the reaction mixture was ice-cooled and crystals formed were collected by filtration and washed with ether. Recrystallized from methanol to obtain 40.85 g of 8-(α-pyridiniumacetyl)carbostyril chloride ½-hydrate. Colorless needle-like crystals. Melting point: 261.5°–264.0° C. (decomposed).

REFERENCE EXAMPLE 14

32 Grams of 8-(α-pyridiniumacetyl)carbostyril chloride, 300 ml of water and 32 g of sodium hydroxide were mixed together and the mixture was stirred at 80°–90° C. for 5 hours. The reaction mixture was treated with activated carbon and to the mother liquor was added concentrated hydrochlorid acid to adjust the pH to about pH 3–4. The crystals formed were collected by filtration, recrystallized from methanol-chloroform to obtain 20.17 g of 8-carboxycarbostyril. Colorless needle-like crystals. Melting point: over 320° C.

NMR (DMSO) δ=6.57 (d, J=9.5 Hz, 1H), 7.25 (t, J=8.0 Hz, 1H), 7.94 (d,d, J=8.0 Hz), 1.5 Hz, 1H), 7.98 (d, J=9.5 Hz, 1H), 8.14 (d,d, J=8.0 Hz, 1.5 Hz, 1H).

EXAMPLE 1

3.5 Grams of 6-carboxy-3,4-dihydrocarbostyril was dissolved in 30 ml of dimethylformamide, then 2.4 g of triethylamine was added in the solution. Under ice-cooled and stirring condition, 2.75 g of isobutyl chloroformate was added dropwise into the reaction mixture and stirred for 30 minutes. Then at a room temperature under stirring condition, 3.19 g of N-methyl-N-(4-methoxy)-benzylamine was added dropwise to the reaction mixture and stirred for 5 hours. The reaction mixture was concentrated to dryness and extracted with chloroform and 1N-sodium hydroxide aqueous solution. The chloroform layer was washed with water and after dried the chloroform layer, then ether was added to the residue and the crystals thus formed were collected by filtration. Recrystallized from methanol to obtain 1.84 g of 6-[N-methyl-N-(4-methoxybenzyl)carbomoyl]-3,4-dihydrocarbostyril in the form of colorless needle-like crystals. Melting point: 144.5°–146.5° C.

EXAMPLE 2

By a method similar to that of Example 1, following compounds were obtained:

6-[N-Methyl-N-(3,4-methylenedioxybenzyl)carbamoyl]-3,4-dihydrocarbostyril

Colorless prism-like crystals (from ethanol)
Melting point: 170°–171° C.

6-[N-Methyl-N-(4-chlorobenzyl)carbamoyl]-3,4-dihydrocarbostyril

Colorless prism-like crystals (from ethanol)
Melting point: 171.5°–172.5° C.

EXAMPLE 3

127 Milligrams of succinimide 3,4-dihydrocarbostyril-6-carboxylate and 39 mg of diethanolamine were dissolved in 2 ml of dimethylformamide and stirred at room temperature for 24 hours. Water was added to the reaction mixture and extracted with chloroform and the chloroform layer was washed with water and a saurated sodium chloride aqueous solution in this order. After drying the chloroform layer with anhydrous sodium sulfate, the chloroform was removed by distillation under a reduced pressure, then acetone was added to the thus obtained residue to crystallize the product. 48 Milligrams of 6-(diethanolaminocarbonyl)-3,4-dihydrocarbostyril was obtained. Melting point: 131°–134° C.

EXAMPLE 4

30 Milliliters of thionyl chloride was added to 2.2 g of 6-(diethanolaminocarbonyl)-3,4-dihydrocarbostyril and the mixture was stirred at a room temperature for 5 hours, then the reaction mixture was concentrated by distillation under a reduced pressure further 50 ml of benzene was added to the residue. The operation of concentration under a reduced pressure was repeated three times, and 6-{[di-(2-chloroethyl)]-aminocarbonyl}-3,4-dihydrocarbostyril was obtained.

EXAMPLE 5

1.0 Gram of succenimide 3,4-dihydrocarbostyril-6-carboxylate and 0.37 g of morpholine were dissolved in 2 ml of dimethylformamide and stirred at room temperature for 3 hours. Then water was added to the reaction mixture and extracted with chloroform, the chloroform layer was washed with water and a saturated sodium chloride aqueous solution in this order. After drying the chloroform layer with anhydrous sodium sulfate, then chloroform was removed by distillation under a reduced pressure, then acetone was added to the thus obtained residue to crystallize the product. 150 Milligrams of 6-morpholinocarbonyl-3,4-dihydrocarbostyril was obtained. Colorless granular crystals. Melting point: 206°–207° C. (from ethanol).

EXAMPLE 6

127 Milligrams of succinimide 3,4-dihydrocarbostyril-6-carboxylate and 93 mg of benzylpiperazine were dissolved in 2 ml of dimethylformaide and the mixture was stirred at room temperature for 24 hours. Water was added to the reaction mixture and extracted with chloroform, the chloroform layer was washed with water and a saturated sodium chloride aqueous solution. After drying the chloroform layer with anhydrous sodium sulfate, chloroform was removed by distillation under a reduced pressure, then acetone was added to the thus obtained residue to crystallize the product. Recrystallize from ethanol to obtain 130 mg of 6-(4-benzyl-1-piperazinylcarbonyl)-3,4-dihydrocarbostyril. Colorless needle-like crystals. Melting point: 198°–200° C.

By a method similar to that of Example 6, following compounds of Examples 7–108 were obtained:

EXAMPLE 7

6-[4-(2-Phenoxyethyl)-1-piperazinylcarbonyl]-3,4-dihydrocarbostyril monohydrochloride Colorless needle-like crystals
Melting point: 271°–274° C. (decomposed)

EXAMPLE 8

6-[4-(2-Cyanoethyl)-1-piperazinylcarbonyl]-3,4-dihydrocarbostyril monohydrochloride Colorless flake-like crystals
Melting point: 240°–243° C. (decomposed)

EXAMPLE 9

6-(1-Piperazinylcarbonyl)-3,4-dihydrocarbostyril

Colorless flake-like crystals
Melting point: 211.5°–213° C.

EXAMPLE 10

6-[4-(3,4-Dimethoxybenzyl)-1-piperazinylcarbonyl]-3,4-dihydrocarbostyril monohydrochloride Colorless granular crystals
Melting point: 240°–242° C. (decomposed)

EXAMPLE 11

6-[4-(4-Methylbenzyl)-1-piperazinylcarbonyl]-3,4-dihydrocarbostyril monohydrochloride Colorless flake-like crystals
Melting point: 280°–283° C. (decomposed)

EXAMPLE 12

6-[4-(3,4-Dichlorobenzyl)-1-piperazinylcarbonyl]-3,4-dihydrocarbostyril monohydrochloride Colorless flake-like crystals
Melting point: 284°–287° C. (decomposed)

EXAMPLE 13

6-[4-(4-Methoxybenzyl)-1-piperazinylcarbonyl]-3,4-dihydrocarbostyril monohydrochloride Colorless granular crystals
Melting point: 262°–264° C. (decomposed)

EXAMPLE 14

6-[4-(4-Chlorobenzyl)-1-piperazinylcarbonyl]-3,4-dihydrocarbostyril monohydrochloride Colorless needle-like crystals
Melting point: over 300° C.

EXAMPLE 15

6-[4-(4-Nitrobenzyl)-1-piperazinylcarbonyl]-3,4-dihydrocarbostyril monohydrochloride ½-hydrate Light yellow granular crystals
Melting point: 268°–271° C. (decomposed)

EXAMPLE 16

6-[4-(3,4-Dimethoxybenzoyl)-1-piperazinylcarbonyl]-3,4-dihydrocarbostyril

Colorless granular crystals
Melting point: 238°–239.5° C.

EXAMPLE 17

6-[4-(4-Cyanobenzoyl)-1-piperazinylcarbonyl]-3,4-dihydrocarbostyril

Colorless needle-like crystals
Melting point: 294°–297° C.

EXAMPLE 18

6-[4-(4-Methoxybenzoyl)-1-piperazinylcarbonyl]-3,4-dihydrocarbostyril

Colorless powdery crystals
Melting point: 247°–249° C.

EXAMPLE 19

6-[4-(3-Chlorobenzoyl)-1-piperazinylcarbonyl]-3,4-dihydrocarbostyril

Colorless powdery crystals
Melting point: 258.5°–260° C.

EXAMPLE 20

6-[4-(4-Bromobenzoyl)-1-piperazinylcarbonyl]-3,4-dihydrocarbostyril

Colorless powdery crystals
Melting point: 265.5°–267.5° C.

EXAMPLE 21

6-[4-(3,4-Dichlorobenzoyl)-1-piperazinylcarbonyl]-3,4-dihydrocarbostyril

Colorless granular crystals
Melting point: 265°–267° C. (decomposed)

EXAMPLE 22

6-[4-(4-Nitrobenzoyl)-1-piperazinylcarbonyl]-3,4-dihydrocarbostyril

Light yellow granular crystals
Melting point: 287°–289° C. (decomposed)

EXAMPLE 23

6-[4-(4-Methylbenzoyl)-1-piperazinylcarbonyl]-3,4-dihydrocarbostyril

Colorless flake-like crystals
Melting point: 262°–264.5° C.

EXAMPLE 24

6-(4-Carbamoylmethyl-1-piperazinylcarbonyl)-3,4-dihydrocarbostyril

Colorless granular crystals
Melting point: 243.5°–244° C.

EXAMPLE 25

6-(4-Methyl-1-piperazinylcarbonyl)-3,4-dihydrocarbostyril monohydroiodide

Colorless powdery crystals
Melting point: 258°–259.5° C. (decomposed)

EXAMPLE 26

6-{4-[(4-Chlorophenyl)(phenyl)methyl]-1-piperazinylcarbonyl}-3,4-dihydrocarbostyril ½-hydrate Colorless powdery crystals
Melting point: 199°–202° C. (decomposed)

EXAMPLE 27

6-[4-(p-Toluenesulfonyl)-1-piperazinylcarbonyl]-3,4-dihydrocarbostyril

Colorless granular crystals
Melting point: 280°–282° C.

EXAMPLE 28

6-(4-Methanesulfonyl-1-piperazinylcarbonyl)-3,4-dihydrocarbostyril

Colorless needle-like crystals
Melting point: 115°–116.5° C.

EXAMPLE 29

6-(4-Ethoxycarbonyl-1-piperazinylcarbonyl)-3,4-dihydrocarbostyril

Colorless powdery crystals
Melting point: 180°–182° C.

EXAMPLE 30

6-(4-n-Hexyl-1-piperazinylcarbonyl)-3,4-dihydrocarbostyril monohydrochloride

Colorless flake-like crystals
Melting point: 276°–280° C. (decomposed)

EXAMPLE 31

6-(4-Cyclohexylmethyl-1-piperazinylcarbonyl)-3,4-dihydrocarbostyril monohydrochloride Colorless flake-like crystals
Melting point: over 300° C.

EXAMPLE 32

6-(4-Isobutyl-1-piperazinylcarbonyl)-3,4-dihydrocarbostyril monohydrochloride

Colorless flake-like crystals
Melting point: 292°–293.5° C. (decomposed)

EXAMPLE 33

6-(4-Allyl-1-piperazinylcarbonyl)-3,4-dihydrocarbostyril monohydrochloride

Colorless flake-like crystals
Melting point: 235°–238° C. (decomposed)

EXAMPLE 34

6-(4-Propargyl-1-piperazinylcarbonyl)-3,4-dihydrocarbostyril monohydrochloride

Colorless granular crystals
Melting point: 249°–251° C. (decomposed)

EXAMPLE 35

6-[4-(4-Methylthiobenzyl)-1-piperazinylcarbonyl]-3,4-dihydrocarbostyril monohydrochloride Colorless granular crystals
Melting point: 264°–268° C. (decomposed)

EXAMPLE 36

6-[4-(3-Phenoxypropyl)-1-piperazinylcarbonyl]-3,4-dihydrocarbostyril monohydrochloride Colorless powdery crystals
Melting point: 151°–153° C. (decomposed)

EXAMPLE 37

6-[4-(6-Phenoxyhexyl)-1-piperazinylcarbonyl]-3,4-dihydrocarbostyril monohydrochloride Colorless powdery crystals
Melting point: 254°–257° C. (decomposed)

EXAMPLE 38

6-[4-(2-Phenylethyl)-1-piperazinylcarbonyl]-3,4-dihydrocarbostyril monohydrochloride ½-hydrate Colorless powdery crystals
Melting point: 269°–272° C. (decomposed)

EXAMPLE 39

6-[4-(3-Phenylpropyl)-1-piperazinylcarbonyl]-3,4-dihydrocarbostyril monohydrochloride ½-hydrate Colorless powdery crystals
Melting point: 257°–259° C. (decomposed)

EXAMPLE 40

6-[4-(4-Aminobenzyl)-1-piperazinylcarbonyl]-3,4-dihydrocarbostyril

Colorless granular crystals
Melting point: 213.5°–214.5° C.

EXAMPLE 41

6-[4-(4-Acetylaminobenzyl)-1-piperazinylcarbonyl]-3,4-dihydrocarbostyril monohydrochloride 3/2-hydrate Colorless powdery crystals
Melting point: 229°–231.5° C.

EXAMPLE 42

6-[4-(3,4,5-Trimethoxybenzoyl)-1-piperazinylcarbonyl]-3,4-dihydrocarbostyril

Colorless powdery crystals
Melting point: 174°–176° C. (decomposed)

EXAMPLE 43

1-Methyl-6-(4-benzyl-1-piperazinylcarbonyl)-3,4-dihydrocarbostyril

Colorless flake-like crystals
Melting point: 145°–146° C.

EXAMPLE 44

1-Allyl-6-[4-(2-phenoxyethyl)-1-piperazinylcarbonyl]-3,4-dihydrocarbostyril monohydrochloride Colorless powdery crystals
Melting point: 239°–241° C.

EXAMPLE 45

1-Benzyl-6-[4-(2-phenoxyethyl)-1-piperazinylcarbonyl]-3,4-dihydrocarbostyril monohydrochloride Colorless powdery crystals
Melting point: 261°–264° C.

EXAMPLE 46

1-Propargyl-6-[4-(3-phenoxypropyl)-1-piperazinylcarbonyl]-3,4-dihydrocarbostyril monohydrochloride Light yellow powdery crystals
Melting point: 137°–139° C. (decomposed)

EXAMPLE 47

6-[4-(2-Furoyl)-1-piperazinylcarbonyl]-3,4-dihydrocarbostyril

Colorless powdery crystals
Melting point: 181°–183.5° C.

EXAMPLE 48

6-(4-Formyl-1-piperazinylcarbonyl)-3,4-dihydrocarbostyril

Colorless powdery crystals
Melting point: 198°–201° C. (decomposed)

EXAMPLE 49

6-[4-(3,4,5-Trimethoxybenzyl)-1-piperazinylcarbonyl]-3,4-dihydrocarbostyril monohydrochloride Colorless needle-like crystals
Melting point: 160°–164° C.

EXAMPLE 50

6-[4-(3,4-Methylenedioxybenzoyl)-1-piperazinylcarbonyl]-3,4-dihydrocarbostyril

Colorless powdery crystals
Melting point: 251°–255° C. (decomposed)

EXAMPLE 51

6-[4-(2-Hydroxyethyl)-1-piperazinylcarbonyl]-3,4-dihydrocarbostyril dihydrate

Colorless rhombic crystals
Melting point: 277°–279° C. (decomposed)

EXAMPLE 52

6-(4-Cyclohexyl-1-piperazinylcarbonyl)-3,4-dihydrocarbostyril

Colorless needle-like crystals
Melting point: 170°–172.5° C.

EXAMPLE 53

6-[4-(3,4-Methylenedioxybenzyl)-1-piperazinylcarbonyl]-3,4-dihydrocarbostyril monohydroochloride Colorless flake-like crystals
Melting point: 277°–279° C. (decomposed)

EXAMPLE 54

6-(1-Piperidylcarbonyl)-3,4-dihydrocarbostyril

Colorless powdery crystals
Melting point: 173°–174° C.

EXAMPLE 55

6-(4-Methyl-1-piperidylcarbonyl)-3,4-dihydrocarbostyril

Colorless rhombic crystals
Melting point: 212°–213.5° C.

EXAMPLE 56

6-(4-Benzyl-1-piperidylcarbonyl)-3,4-dihydrocarbostyril ½-hydrate

Colorless powdery crystals
Melting point: 235°–236.5° C.

EXAMPLE 57

6-(1-Pyrrolidylcarbonyl)-3,4-dihydrocarbostyril

Colorless needle-like crystals
Melting point: 200°–202° C.

EXAMPLE 58

6-[4-(4-Phenoxybutyl)-1-piperazinylcarbonyl]-3,4-dihydrocarbostyril monohydrochloride Colorless granular crystals
Melting point: 250°–252° C.

EXAMPLE 59

6-{4-[3-(3-Chlorophenoxy)propyl]-1-piperazinylcarbonyl}-3,4-dihydrocarbostyril monohydrochloride Colorless needle-like crystals
Melting point: 254°–256.5° C. (decomposed)

EXAMPLE 60

6-4-[3-(2-Chlorophenoxy)propyl]-1-piperazinylcarbonyl-3,4-dihydrocarbostyril monohydrochloride Colorless powdery crystals
Melting point: 256°–258° C.

EXAMPLE 61

6-{4-[3-(4-Methylphenoxy)propyl]-1-piperazinylcarbonyl}-3,4-dihydrocarbostyril monohydrochloride Colorless flake-like crystals
Melting point: 265°–266.5° C. (decomposed)

EXAMPLE 62

6-{4-[2-(4-Methoxyphenoxy)ethyl]-piperazinylcarbonyl}-3,4-dihydrocarbostyril monohydrochloride Colorless needle-like crystals
Melting point: 270°–272° C. (decomposed)

EXAMPLE 63

6-{4-[2-(3,4-Methylenedioxyphenoxy)ethyl]-1-piperazinylcarbonyl}-3,4-dihydrocarbostyril monohydrochloride Colorless needle-like crystals
Melting point: 164°–166° C. (decomposed)

EXAMPLE 64

6-{4-[2-(3-Chorophenoxy)ethyl]-1-piperazinylcarbonyl}-3,4-dihydrocarbostyril monohydrochloride Colorless powdery crystals
Melting point: 249°–251.5° C.

EXAMPLE 65

6-[4-(Benzoylmethyl)-1-piperazinylcarbonyl]-3,4-dihydrocarbostyril monohydrochloride ½-hydrate Colorless powdery crystals
Melting point: 212°–215° C.

EXAMPLE 66

6-{4-[(4-Methoxybenzoyl)methyl]-1-piperazinylcarbonyl}-3,4-dihydrocarbostyril monohydrochloride Colorless powdery crystals
Melting point: 266.5°–269° C. (decomposed)

EXAMPLE 67

6-{4-[(4-Chlorobenzoyl)methyl]-1-piperazinylcarbonyl}-3,4-dihydrocarbostyril monohydrochloride ½-hydrate Colorless flake-like crystals
Melting point: 242°–245° C. (decomposed)

EXAMPLE 68

6-{4-[(3-Chlorobenzoyl)methyl]-1-piperazinylcarbonyl}-3,4-dihydrocarbostyril monohydrochloride ½-hydrate Colorless powdery crystals
Melting point: 143.5°–146° C. (decomposed)

EXAMPLE 69

6-{4-[(4-Methylbenzoyl)methyl]-1-piperazinylcarbonyl}-3,4-dihydrocarbostyril monohydrochloride Colorless powdery crystals
Melting point: 270°–272° C. (decomposed)

EXAMPLE 70

6-{4-[(4-Hydroxybenzoyl)methyl]-1-piperazinylcarbonyl}-3,4-dihydrocarbostyril monohydrochloride ½-hydrate Colorless powdery crystals
Melting point: 162°–164° C.

EXAMPLE 71

6-[4-(2-Benzoylethyl)-1-piperazinylcarbonyl]-3,4-dihydrocarbostyril monohydrochloride Colorless flake-like crystals
Melting point: 205°–207° C. (decomposed)

EXAMPLE 72

6-[4-(3-Benzoylpropyl)-1-piperazinylcarbonyl]-3,4-dihydrocarbostyril monohydrochloride ½-hydrate Colorless needle-like crystals
Melting point: 241°–242.5° C.

EXAMPLE 73

6-[4-(5-Benzoylpentyl)-1-piperazinylcarbonyl]-3,4-dihydrocarbostyril monohydrochloride monohydrate Colorless powdery crystals
Melting point: 239°–242° C.

EXAMPLE 74

6-{4-[3-(4-Ethylbenzoyl)propyl]-1-piperazinylcarbonyl}-3,4-dihydrocarbostyril monohydrochloride ½-hydrate Colorless powdery crystals
Melting point: 230°–233° C. (decomposed)

EXAMPLE 75

6-{4-[3-(4-Chlorobenzoyl)propyl]-1-piperazinylcarbonyl}-3,4-dihydrocarbostyril monohydrochloride ½-hydrate Colorless powdery crystals
Melting point: 238°–240° C.

EXAMPLE 76

6-{4-[3-(3,4-Dimethoxybenzoyl)propyl]-1-piperazinylcarbonyl}-3,4-dihydrocarbostyril monohydrochloride ½-hydrate Colorless powdery crystals
Melting point: 225°–228° C.

EXAMPLE 77

6-{4-[2-(4-Methylbenzoyl)ethyl]-1-piperazinylcarbonyl}-3,4-dihydrocarbostyril

Colorless flake-like crystals
Melting point: 224.5°–226° C. (decomposed)

EXAMPLE 78

6-{4-[2-(4-Methoxybenzoyl)ethyl]-1-piperazinylcarbonyl}-3,4-dihydrocarbostyril monohydrochloride monohydrate Colorless rhombic crystals
Melting point: 204°–205° C. (decomposed)

EXAMPLE 79

6-{4-[2-(4-Acetylaminobenzoyl)ethyl]-1-piperazinylcarbonyl}-3,4-dihydrocarbostyril Colorless powdery crystals
Melting point: 207°–209° C. (decomposed)

EXAMPLE 80

6-[4-(3-Chlorocinnamoyl)-1-piperazinylcarbonyl]-3,4-dihydrocarbostyril ¼-hydrate Colorless granular crystals
Melting point: 239.5°–241.5° C.

EXAMPLE 81

6-[4-(3,4,5-Trimethoxycinnamoyl)-1-piperazinylcarbonyl]-3,4-dihydrocarbostyril

Colorless granular crystals
Melting point: 281°–284° C.

EXAMPLE 82

6-(4-Acetylmethyl-1-piperazinylcarbonyl)-3,4-dihydrocarbostyril monohydrochloride ½-hydrate Colorless powdery crystals
Melting point: 225°–227° C. (decomposed)

EXAMPLE 83

6-[4-(2-Hydroxypropyl)-1-piperazinylcarbonyl]-3,4-dihydrocarbostyril

Colorless flake-like crystals
Melting point: 156°–157.5° C.

EXAMPLE 84

6-[4-(2-Acetyloxypropyl)-1-piperazinylcarbonyl]-3,4-dihydrocarbostyril monohydrochloride ½-hydrate Colorless powdery crystals
Melting point: 239°–241° C. (decomposed)

EXAMPLE 85

6-{4-[3,4,5-Trimethoxybenzoyloxy)propyl]-1-piperazinylcarbonyl}-3,4-dihydrocarbostyril monohydrochloride Colorless powdery crystals
Melting point: 220°–222° C. (decomposed)

EXAMPLE 86

6-{4-[2-(3,4-Dimethoxybenzyloxy)ethyl]-1-piperazinylcarbonyl}-3,4-dihydrocarbostyril monohydrochloride Colorless rhombic crystals
Melting point: 240°–242° C. (decomposed)

EXAMPLE 87

6-(1-Piperazinylcarbonyl)carbostyril monohydrochloride

Colorless granular crystals
Melting point: over 300° C.

EXAMPLE 88

6-(4-Benzyl-1-piperazinylcarbonyl)carbostyril monohydrochloride monohydrate

Colorless granular crystals
Melting point: over 300° C.

EXAMPLE 89

6-[4-(3-Chlorobenzoyl)-1-piperazinylcarbonyl]carbostyril

Colorless powdery crystals
Melting point: over 300° C.

EXAMPLE 90

6-[4-(2-Phenoxyethyl)-1-piperazinylcarbonyl]carbostyril monohydrochloride

Colorless powdery crystals
Melting point: 286°–289° C. (decomposed)

EXAMPLE 91

6-[4-(3-Phenylpropyl)-1-piperazinylcarbonyl]carbostyril monohydrochloride

Colorless powdery crystals
Melting point: 290°–293° C. (decomposed)

EXAMPLE 92

6-[4-(4-Methylbenzyl)-1-piperazinylcarbonyl]carbostyril monohydrochloride

Colorless powdery crystals
Melting point: over 300° C.

EXAMPLE 93

6-(4-Isobutyl-1-piperazinylcarbonyl)carbostyril monohydrochloride ½-hydrate

Colorless powdery crystals
Melting point: over 300° C.

EXAMPLE 94

6-[4-(3,4-Dichlorobenzyl)-1-piperazinylcarbonyl]carbostyril monohydrochloride ½-hydrate Colorless powdery crystals
Melting point: over 300° C.

EXAMPLE 95

6-[4-(4-Chlorobenzyl)-1-piperazinylcarbonyl]carbostyril monohydrochloride

Colorless needle-like crystals
Melting point: over 300° C.

EXAMPLE 96

5-(4-Isobutyl-1-piperazinylcarbonyl)carbostyril monohydrochloride ½-hydrate

Colorless powdery crystals
Melting point: 251°–254° C. (decomposed)

EXAMPLE 97

5-[4-(2-Phenoxyethyl)-1-piperazinylcarbonyl]carbostyril monohydrochloride

Colorless powdery crystals
Melting point: 227°–229° C.

EXAMPLE 98

5-[4-(2-Benzoylethyl)-1-piperazinylcarbonyl]carbostyril monohydrochloride ½-hydrate Colorless powdery crystals
Melting point: 181.5°–184° C.

EXAMPLE 99

5-[4-(3-Phenylpropyl)-1-piperazinylcarbonyl]carbostyril monohydrochloride

Colorless powdery crystals
Melting point: 226°–228.5° C.

EXAMPLE 100

5-[4-(3,4-Methylenedioxybenzyl)-1-piperazinylcarbonyl]carbostyril monohydrochloride ½-hydrate Colorless powdery crystals
Melting point: 236°–239° C. (decomposed)

EXAMPLE 101

6-(2-Methyl-1-piperidylcarbonyl)-3,4-dihydrocarbostyril

Colorless powdery crystals
Melting point: 162°–164° C.

EXAMPLE 102

7-(4-Benzyl-1-piperazinylcarbonyl)-3,4-dihydrocarbostyril monohydrochloride

Colorless rhombic crystals
Melting point: 260°–262° C. (decomposed)

EXAMPLE 103

7-(4-Isobutyl-1-piperazinylcarbonyl)-3,4-dihydrocarbostyril monohydrochloride ½-hydrate Colorless powdery crystals
Melting point: 262°–264° C. (decomposed)

EXAMPLE 104

7-[4-(2-Benzoylethyl)-1-piperazinylcarbonyl]-3,4-dihydrocarbostyril monohydrochloride ½-hydrate Colorless rhombic crystals
Melting point: 205°–208° C. (decomposed)

EXAMPLE 105

7-[4-(2-Phenoxyethyl)-1-piperazinylcarbonyl]-3,4-dihydrocarbostyril monohyrochloride Colorless flake-like crystals
Melting point: 177°–180° C.

EXAMPLE 106

8-(4-Isobutyl-1-piperazinylcarbonyl)carbostyril monohydrochloride

Colorless powdery crystals
Melting point: 251°–254° C. (decomposed)

EXAMPLE 107

8-[4-(2-Benzoylethyl)-1-piperazinylcarbonyl]carbostyril

Colorless powdery crystals
Melting point: 182°–184° C.

EXAMPLE 108

8-[4-(3-Phenylpropyl)-1-piperazinylcarbonyl]carbostyril

Colorless powdery crystals
Melting point: 195°–196° C.

EXAMPLE 109

0.64 Gram of β-chlorophenethol and 0.61 g of sodium iodide were suspended in 7 ml of dimethylformamide and the mixture was stirred at a room temperature for 30 minutes. Then to this mixture were added 1.0 g of 6-(1-piperazinylcarbonyl)carbostyril monohydrochloride and 1.2 g of potassium carbonate and the mixture was stirred at 70°–80° C. for 12 hours. The reaction mixture was poured into 1N-sodium hydroxide aqueous solution and was extracted with chloroform. The chloroform layer was washed with water and a saturated sodium chloride aqueous solution in this order and dried with anhydrous sodium sulfate. After removal of the solvent by distillation, the residue was dissolved in methanol and the pH was a adjusted to about pH 1 by adding concentrated hydrochloric acid. After removal of the solvent by distillation, the residue was recrystallized from ethanol-water to obtain 0.84 g of 6-[4-(2-phenoxyethyl)-1-piperazinylcarbonyl]carbostyril monohydrochloride. Colorless powdery crystals. Melting point: 286°–289° C. (decomposed)

EXAMPLE 110

3.0 Grams of 6-(1-piperazinylcarbonyl)-3,4-dihydrocarbostyril, 2.9 g of triethylamine, 2.7 g of β-chlorophenethol and 2.1 g of sodium iodide were suspended in a mixed solvent of 20 ml of acetonitrile with 20 ml of dimethylformamide, and the reaction mixture was refluxed for 15 hours under stirring condition. Then the solvents were removed by distillation, and the residue thus obtained was extracted with a mixed solvent of a saturated sodium bicarbonate aqueous solution with chloroform, the organic layer was washed with water and a saturated sodium chloride aqueous solution in this order, then the extract was dried with anhydrous sodium sulfate, and the solvent was removed by distillation under a reduced pressure. To the thus obtained residue was added concentrated hydrochloric acid to adjust the pH of the residue to about pH 1 so as to obtain the hydrochloride. Recrystallized from ethanol-water to obtain 2.13 g of 6-[4-(2-phenoxyethyl)-1-piperazinylcarbonyl]-3,4-dihydrocarbostyril monohydrochloride. Colorless needle-like crystals. Melting point: 271°–274° C. (decomposed).

By methods similar to those described in Examples 109 and 110 and using suitable starting materials, there were obtained compounds of Examples 8, 24, 25, 36, 37, 44, 45, 46, 51, 52, 58–79, 82–86, 90, 91, 93, 96–99, 103–108.

EXAMPLE 111

1.0 Gram of 6-(1-piperazinylcarbonyl)carbostyril-monohydrochloride, 0.7 g of p-chlorobenzylchloride and 1.4 ml of triethylamine were suspended in 15 ml of acetonitrile and stirred at 50°–70° C. for 4 hours. Then the reaction was continued on an ice bath for 1 hour so as to form crystals in the reaction mixture. Thus formed crystals were collected by filtration and extracted with chloroform-saturated sodium bicarbonate aqueous solution, the chloroform layer was washed with water and a saturated sodium chloride aqueous solution in this order and dried with anhydrous sodium sulfate. The solvent was removed by distillation under a reduced pressure and the residue thus obtained was dissolved in methanol and the pH of the methanol solution was adjusted to about pH 1 by adding concentrated hydrochloric acid. Crude crystals were recrystallized from ethanol-water to obtain 0.73 g of 6-[4-(4-chlorobenzyl)-1-piperazinyl-carbonyl]carbostyril monohydrochloride. Colorless needle-like crystals. Melting point: over 300° C.

EXAMPLE 112

2.6 Grams of 6-(1-piperazinylcarbonyl)-3,4-dihydrocarbostyril, 3.0 g of triethylamine and 2.9 g of 3,4-dimethoxybenzylchloride were suspended in acetonitrile and the suspension was stirred at 50°–55° C. for 2 hours. After removal of the solvent the residue thus obtained was extracted with chloroform, and the chloroform extract was washed with water and a saturated sodium chloride aqueous solution in this order, dried with anhydrous sodium sulfate. The solvent was removed by distillation and the pH of thus obtained residue was adjusted by adding concentrated hydrochloric acid to about pH 1 so as to form the hydrochloride of the product. Recrystallized from methanol-water to obtain 1.50 g of 6-[4-(3,4-dimethoxybenzyl)-1-piperazinylcarbonyl]-3,4-dihydrocarbostyril monohydrochloride. Colorless granular crystals. Melting point: 240°–242° C. (decomposed)

By methods similar to those described in Examples 111 and 112 and using suitable starting materials, there were obtained compounds of Examples 6, 11–15, 25, 26, 30–41, 43–46, 49, 53, 88, 91, 92, 94, 95, 99, 100, 102 and 108.

EXAMPLE 113

1.0 Gram of 6-(1-piperazinylcarbonyl)carbostyril monohydrochloride, 0.72 g of m-chlorobenzoylchloride and 1.4 ml of triethylamine were suspended in 15 ml of dichloromethane and the suspension was stirred at a room temperature for 2 hours. Crystals formed in the reaction mixture were collected by filtration and recrystallized from dimethylformamide to obtain 1.07 g of 6-[4-(3-chlorobenzoyl)-1-piperazinylcarbonyl]-carbostyril. Colorless powdery crystals. Melting point: over 300° C.

EXAMPLE 114

3.0 Grams of 6-(1-piperazinylcarbonyl)-3,4-dihydrocarbostyril and 4.0 ml of tiethylamine were suspended in 20 ml of dichloromethane, and to the suspension was added dropwise 3.5 g of 3,4-dimethoxybenzoylchloride in 20 ml of dichloromethane under ice-cooled condition with stirring. Then the reaction was continued for additional 1 hour at a room temperature. The reaction mixture was poured into a saturated sodium bicarbonate aqueous solution and extracted with chloroform. The chloroform layer was washed with water and a saturated sodium chloride aqueous solution in this order and was dried with anhydrous sodium sulfate, and the solvent was removed by distillation. The residue thus obtained was recrystallized from ethanol-chloroform to obtain 4.1 g of 6-[4-(3,4-dimethoxybenzoyl)-1-piperazinylcarbonyl]-3,4-dihydrocarbostyril. Colorless granular crystals. Melting point: 238°–239.5° C.

By methods similar to those described in Examples 113 and 114 and using suitable starting materials, there were obtained compounds of Examples 17–23, 29, 42, 47, 48, 50, 80, 81 and 89.

EXAMPLE 115

1.5 Grams of 6-(1-piperazinylcarbonyl)-3,4-dihydrocarbostyril and 1.5 g of triethylamine were suspended in 10 ml of dichloromethane. Under ice-cooled and stirring condition, 1.4 g of p-toluenesulfonylchloride in 10 ml of dichloromethane solution was added dropwise to the suspension and the reaction was continued for additionally 3 hours at a room temperature, further continued for 1 hour under ice-cooled condition. The crystals formed in the reaction mixture were collected by filtration and recrystallized from chloroform-ether to obtain 1.4 g of 6-[4-(p-toluenesulfonyl)-1- piperazinylcarbonyl]-3,4-dihydrocarbostyril. Colorless granular crystals. Melting point: 280°-282° C.

By a method similar to that described in Exmple 115 and using a suitable starting material, there was obtained a compound of Example 28.

EXAMPLE 116

2.62 Grams of 6-morpholinocarbonyl-3,4-dihydrocarbostyril and 17.9 g of 3,4-dimethoxybenzylamine were placed in a sealed tube and heated at 170°-200° C. for 5 hours. Then 3,4-dimethoxybenzylamine was removed by distillation under a reduced pressure and the residue thus obtained was treated by means of a silica gel column chromatography, and the objective product was changed to a hydrochloride by adding concentrated hydrochloric acid. Recrystallized from methanol-water to obtain 0.35 g of 6-[4-(3,4-dimethoxybenzyl)-1-piperazinylcarbonyl]-3,4-dihydrocarbostyril monohydrochloride. Colorless granular crystals. Melting point: 240°-242° C. (decomposed)

By a method similar to that described in Example 116, and using a suitable starting material there were obtained compounds of Examples 6-8, 11-15, 24, 25, 26, 30-41, 43-46, 49, 51-53, 58-79, 82-86 and 90-108.

EXAMPLE 117

A mixture of 10 g of 6-[bis-(2-hydroxyethyl)aminocarbonyl]-3,4-dihydrocarbostyril, 4.5 g of 3,4-dimethoxybenzylamine and 7.6 g of a polyphosphoric acid was heated at 160°-170° C. for about 6 hours to be reacted. After the reaction was completed, the reaction mixture was allowed to cooled and 500 ml of water was added thereto to dissolve. The solution was neutralized with 48% of sodium hydroxide solution and extracted with chloroform. The chloroform extract was dried with anhydrous potassium carbonate, the chloroform was removed by distillation, then to the residue thus obtained was added concentrated hydrochloric acid so as to form the objective product into the hydrochloride. Recrystallized from methanol-water to obtain 7.5 g of 6-[4-(3,4-dimethoxybenzyl)-1-piperazinylcarbonyl]-3,4-dihydrocarbostyril monohydrochloride. Colorless granular crystals. Melting point: 240°-242° C. (decomposed)

By a method similar to that described in Example 117 and using suitable starting materials, there were obtained compounds of Examples 1-8, 11-15, 24-26, 30-41, 43-46, 49, 51-53, 58-79, 82-86 and 90-108.

EXAMPLE 118

A mixture of 15.9 g of 6-[bis-(2-chloroethyl)aminocarbonyl]-3,4-dihydrocarbostyril, 9.8 g of 3,4-dimethoxybenzylamine and 70 ml of methanol was refluxed with stirring for 15 hours. After the reaction was completed, the reaction mixture was cooled, then 3.06 g of sodium carbonate was added to the mixture and refluxed with stirring for 8 hours. After cooling the mixture, crystals formed were collected by filtration, and the hydrochloride was formed by adding concentrated hydrochloric acid. Recrystallized from methanol-water to obtain 7.3 g of 6-[4-(3,4-dimethoxybenzyl)-1-piperazinylcarbonyl]-3,4-dihydrocarbostyril monohydrochloride. Colorless granular crystals. Melting point: 240°-242° C. (decomposed)

By a method similar to that described in Example 118, and using a suitable starting material, there were obtained compounds of Examples 1-8, 11-15, 24-26, 30-41, 43-46, 49, 51-53, 58-79, 82-86 and 90-108.

EXAMPLE 119

1.0 Gram of 6-carboxy-3,4-dihydrocarbostyril, 1.3 g of DCC and 1.1 g of benzylpiperazine were suspended in 10 ml of dioxane and the suspension was stirred at 70° C. for 5 hours. After the reaction was completed, the solvent was removed by distillation and ether was added to the residue and crystals formed were removed by filtration. After the mother liquor was concentrated, the residue was dissolved in chloroform and the chloroform solution was washed with water and a saturated sodium chloride aqueous solution then dried with anhydrous sodium sulfate and the solvent was removed by distillation. Recrystallized from ethanol to obtain 330 mg of 6-(4-benzyl-1-piperazinylcarbonyl)-3,4-dihydrocarbostyril. Colorless needle-like crystals. Melting point: 198°-200° C.

By a method similar to that described in Example 119, and using a suitable starting material, there were obtained compounds of Examples 1, 2, 3, 4, 5 and 7-108.

EXAMPLE 120

1.0 Gram of 6-carboxy-3,4-dihydrocarbostyril and 0.8 ml of triethylamine were suspended in 10 ml of tetrahydrofuran, and under stirring at a room temperature condition, 1.0 g of diethylchlorophosphate in 10 ml of tetrahydrofuran solution was added dropwise to the suspension, and stirred at room temperature for 3 hours. To this reaction mixture, 1.1 g of benzylpiperazine in 10 ml of tetrahydrofuran solution was added dropwise then stirred at a room temperature for 10 hours. After the reaction was completed, the crystals formed in the reaction mixture were removed by filtration and the mother liquor was concentrated, and to the residue thus obtained was poured a saturated sodium bicarbonate aqueous solution and then extracted with chloroform. The organic layer was washed with water and a saturated sodium chloride aqueous solution then dried with anhydrous sodium sulfate and the solvent was removed by distillation. Recrystallized from ethanol 1.07 g of 6-(4-benzyl-1-piperazinylcarbonyl)-3,4-dihydrocarbostyril. Colorless needle-like crystals. Melting point: 198°-200° C.

By a method similar to that described in Example 120, and using a suitable starting material, there were obtained compounds of Examples 1, 2, 3, 4, 5, 7-108.

EXAMPLE 121

34.5 Grams of 6-carboxycarbostyril and 31 ml of triethylamine were dissolved in 350 ml of dimethylformamide and stirred at a room temperature. Then 28 ml of isobutyl chloroformate in 14 ml of dimethylformamide solution was added dropwise to the former solution. After stirring at a room temperature for 1 hour, 37 g of benzylpiperazine in 21 ml of dimethylformamide solution was added dropwise to the reaction mixture and stirred at a room temperature for 10 hours. The reaction mixture was poured into a saturated sodium bicarbonate aqueous solution, then extracted with chloroform. The chloroform layer was washed with water and a saturated sodium chloride aqueous solution in this order and the chloroform extract was dried with anhydrous sodium sulfate. The solvent was removed by distillation under a reduced pressure, the residue thus obtained was crystallized by adding ether and the crystals were collected by filtration. The crystals were dissolved in methanol and the pH of the solution was adjusted to about pH 1 by adding concentrated hydrochloric acid. The crude crystals thus obtained were recrystallized from ethanol-water to obtain 30.1 g of 6-(4-benzyl-1-piperazinylcarbonyl)carbostyril monohydrochloride monohydrate. Colorless granular crystals. Melting point: over 300° C.

EXAMPLE 122

To a solution of 50 ml of dimethylformamide with 5.0 g of 6-carboxy-3,4-dihydrocarbostyril and 4 ml of triethylamine, 3.87 g of isobutyl chloroformate in 2 ml of dimethylformamide solution was added dropwise. After stirring at a room temperature for 30 minutes, 5.5 g of benzylpiperazine in 3 ml of dimethylformamide solution was added to the former solution and stirred at a room temperature for 30 minutes, then stirred continuously at 50°–60° C. for 1 hour. The reaction mixture was poured into a voluminous amount of a saturated sodium chloride aqueous solution and extracted with chloroform and the chloroform extract was washed with water and dried. After removal of the solvent, to the residue thus obtained was added diethyl ether to crystallize the residue and recrystallized from ethanol to obtain 3.4 g of 6-(4-benzyl-1-piperazinylcarbonyl)-3,4-dihydrocarbostyril. Colorless needle-like crystals. Melting point: 198°–200° C.

By methods similar to those described in Examples 121 and 122 by using a suitable starting material, there were obtained compounds of Examples 3, 4, 5, 7–87 and 89–108.

EXAMPLE 123

To 100 ml of ethanol was added 2.0 g of 6-ethoxycarbonyl-3,4-dihydrocarbostyril, 0.5 g of sodium ethylate and 1.6 g of benzylpiperazine, the mixture was reacted in an autoclave under 110 atmospheric pressure at 140°–150° C. for 6 hours. After the reaction was completed, the reaction mixture was cooled and concentrated under a reduced pressure. The residue thus obtained was dissolved in 200 ml of chloroform and the chloroform solution was washed with 1%-potassium carbonate aqueous solution, a diluted hydrochloric acid and water in this order, then dried with anhydrous sodium sulfate. The solvent was removed by distillation and the residue was treated by means of a silica gel column chromatography (Silica gel: Wako C-200, eluate:chloroform:methanol (volume/volume)=20:1) and the crude crystals were recrystallized from ethanol to obtain 300 mg of 6-(4-benzyl-1-piperazinylcarbonyl)-3,4-dihydrocarbostyril. Colorless needle-like crystals. Melting point: 198°–200° C.

By a method similar to that described in Example 123 by using a suitable starting material, there were obtained compounds of Examples 1–5, 7–108.

EXAMPLE 124

1.9 Grams of 6-carboxy-3,4-dihydrocarbostyril was suspended in 200 ml of methylene chloride, then 2 ml of pyridine was added to the suspension and under stirring 1.4 g of thionyl chloride was added dropwise in keeping the inside temperature at 0°–20° C. After the addition of thionyl chloride, the reaction mixture was kept at the same temperature and stirred for 1 hour, then 1.74 g of benzylpiperazine in 10 ml of methylene chloride solution was added to the mixture. Then the reaction mixture was further stirred at a room temperature for 4 hours. The reaction mixture was washed thoroughly with an aqueous solution of potassium carbonate, then washed with water and a diluted hydrochloric acid, dried with anhydrous sodium sulfate and the solvent was removed by distillation. The residue thus obtained was treated by a silica gel column chromatography (Silica gel: Wako C-200, eluate:chloroform:methanol (volume/volume)=20:1). The objective product was recrystallized from ethanol to obtain 325 mg of 6-(4-benzyl-1-piperazinylcarbonyl)-3,4-dihydrocarbostyril. Colorless needle-like crystals. Melting point: 198°–200° C.

By a method similar to that described in Example 124 and using a suitable starting material, there were obtained compounds of Examples 1–5 and 7–108.

EXAMPLE 125

Into 100 ml of dimethylformamide, 2.6 g of 3,4-dimethoxybenzoic acid and 1.65 g of 1,8-diazabicyclo[5,4,0]undecene-7 were added, then the outside of the reaction vessel was ice-cooled and stirring condition, 1.5 ml of isobutyl chloroformate was added dropwise. Then the reaction mixture was further stirred for 30 minutes, a solution of 2.6 g of 6-(1-piperazinyl)carbonyl-3,4-dihydrocarbostyril dissolved in 40 ml of dimethylformamide was added to the reaction mixture and stirred at a room temperature for 5 hours. After the reaction was completed, the solvent was removed by distillation and the residue was extracted with about 300 ml of chloroform, then washed with a diluted sodium hydrogencarbonate aqueous solution, water, a diluted hydrochloric acid and water in this order. After removal of chloroform by distillation, the residue was recrystallized from ethanol-chloroform to obtain 1.8 g of 6-[4-(3,4-dimethoxybenzoyl)-1-piperazinylcarbonyl]-3,4-dihydrocarbostyril. Colorless granular crystals. Melting point: 238°–239.5° C.

By a method similar to that described in Example 125 and using a suitable starting material, there were obtained compounds of Examples 17–23, 29, 42, 47, 48, 50, 80, 81 and 89.

EXAMPLE 126

123 Grams of succinimide 3,4-dimethoxybenzoate and 137 mg of 6-(1-piperazinylcarbonyl)-3,4-dihydrocarbostyril were dissolved in 2 ml of dimethylformamide and stirred for 24 hours. The water was added to the reaction mixture and extracted with chloroform, the chloroform extract was washed with water and a saturated sodium chloride aqueous solution and dried with anhydrous sodium sulfate. The solvent was removed by distillation and the residue was recrystallized from ethanol-chloroform to obtain 100 mg of 6-[4-(3,4-dimethoxybenzoyl)-1-piperazinylcarbonyl]-3,4-dihydrocarbostyril. Colorless granular crystals. Melting point: 238°–239.5° C.

By a method similar to that described in Example 126 and using a suitable starting material, there were obtained compounds of Examples 17–23, 29, 42, 47, 48, 50, 80, 81 and 89.

EXAMPLE 127

To a solution of 4.8 g of 3,4-dimethoxybenzoic acid and 4 ml of triethylamine in 50 ml of dimethylformamide, a solution of 3.87 g of isobutylchloroformate in 2 ml of dimethylformamide was added dropwise. After the reaction mixture was stirred at a room temperature for 30 minutes, then a solution of 8.1 g of 6-(1-piperazinylcarbonyl)-3,4-dihydrocarbostyril in 3 ml of dimethylformamide was added dropwise to the reaction mixture and stirred at a room temperature for 30 minutes, and further stirred at 50°-60° C. for 1 hour. After the reaction was completed, the reaction mixture was poured into a voluminous amount of a saturated sodium chloride aqueous solution and then extracted with chloroform and the chloroform extract was washed with water and dried. The solvent was removed by distillation, and the residue was recrystallized from ethanol-chloroform to obtain 2.5 g of 6-[4-(3,4-dimethoxybenzoyl)-1-piperazinylcarbonyl]-3,4-dihydrocarbostyril. Colorless granular crystals. Melting point: 238°-239.5° C.

By a method similar to that described in Example 127 and using a suitable starting material, there were obtained compounds of Examples 17-23, 29, 42, 47, 48, 50, 80, 81 and 89.

EXAMPLE 128

To 100 ml of ethanol was added 1.9 g of ethyl 3,4-dimethoxybenzoate, 0.5 g sodium ethylate and 2.4 g of 6-(1-piperazinylcarbonyl)-3,4-dihydrocarbostyril, the mixture was reacted in an autoclave under 110 atmospheric pressure at 140°-150° C. for 6 hours. After the reaction was completed, the reaction mixture was cooled and concentrated under a reduced pressure. The residue thus obtained was dissolved in 200 ml of chloroform and the chloroform solution was washed with 1%-potassium carbonate aqueous solution, a dilute hydrochloric acid and water in this order, then dried with anhydrous sodium sulfate. The solvent was removed by distillation and the residue was treated by means of a silica gel column chromatography (Silica gel: Wako C-200, eluent:chloroform:methanol (volume/volume)=20:1) and the crude crystals was recrystallized from ethanol-chloroform to obtain 250 mg of 6-[4-(3,4-dimethoxybenzoyl)-1-piperazinylcarbonyl]-3,4-dihydrocarbostyril. Colorless granular crystals. Melting point: 238°-239.5° C.

By a method similar to that described in Example 128 and using a suitable starting material, there were obtained compounds of Examples 17-23, 29, 42, 47, 48, 50, 80, 81 and 89.

EXAMPLE 129

1.8 Grams of 3,4-dimethoxybenzoic acid and 2.75 g of 6-(1-piperazinylcarbonyl)-3,4-dihydrocarbostyril were added to a mixed solvent of 20 ml of dioxane with 20 ml of methylene chloride. Under the condition that the outside of reaction vessel was ince-cooled with stirring, a solution of 2.1 g of N,N-dicyclohexylcarbodiimide being dissolved in 5 ml of methylene chloride by keeping its temperature to 10°-20° C. was added dropwise thereto and stirred at the same temperature for 3.5 hours. The crystals formed in the reaction mixture were removed by filtration, and the mother liquor was concentrated under a reduced pressure. The residue thus obtained was dissolved in 100 ml of methylene chloride and the organic layer was washed with 5%-hydrochloric acid aqueous solution, 5%-sodium hydrogencarbonate aqueous solution and water in this order, then the organic layer was dried with anhydrous sodium sulfate. The solvent was removed by distillation under a reduced pressure and the residue thus obtained was recrystallized from chloroform-ethanol to obtain 0.9 g of 6-[4-(3,4-dimethoxybenzoyl)-1-piperazinylcarbonyl]-3,4-dihydrocarbostyril. Colorless granular crystals. Melting point: 238°-239.5° C.

By a method similar to that described in Example 129 and using a suitable starting material, there were obtained compounds of Examples 17-23, 29, 42, 47, 48, 50, 80, 81 and 89.

EXAMPLE 130

480 Milligrams of 6-[4-(2-phenoxyethyl)-1-piperazinylcarbonyl]-3,4-dihydrocarbostyril and 70 ml of 50%-sodium hydride in oil were mixed into 5 ml of dimethylformamide and stirred at a room temperature for 1 hour. Then to this mixture was added a solution of 0.17 ml of benzyl chloride with 3 ml of dimethylformamide was added dropwise slowly and stirred at a room temperature for 4 hours. The reaction mixture was poured in a voluminous amount of water and the organic matters were extracted with chloroform, and the chloroform layer was washed with water, dried and chloroform was removed by distillation. The residue obtained was converted into hydrochloride by adding a concentrated hydrochloric acid and recrystallized from methanol-water to obtain 150 mg of 1-benzyl-6-[4-(2-phenoxyethyl)-1-piperazinylcarbonyl]-3,4-dihydrocarbostyril monohydrochloride. Colorless powdery crystals. Melting point: 261°-264° C.

By a method similar to that described in Example 130 and using a suitable starting material, there were obtained compounds of Examples 43, 44 and 46.

EXAMPLE 131

26.4 Grams of 6-[(4-benzyl-1-piperazinyl)carbonyl]-carbostyril was suspended in 800 ml of a mixed solvent of ethanol-water and the pH of the suspension was adjusted to about pH 1 by adding concentrated hydrochloric acid. To this mixture was added 2.6 g of 5% palladium-carbon and catalytic reduction was conducted under a normal pressure at 45°-65° C. After the reaction was completed, the catalyst was removed by filtration and the solvent was removed by distillation under a reduced pressure. The residue obtained was crystallized by adding acetone and the crude crystals thus obtained were recrystallized from ethanol-water to obtain 19.9 g of 6-(1-piperazinylcarbonyl)carbostyril monohydrochloride. Colorless granular crystals. Melting point: over 300° C.

EXAMPLE 132

By method similar to those described in Examples 6, 110, 112, 116, 117, 118, 119, 120, 122, 123 and 124 and using a suitable starting material, there were obtained compounds as follows:

6-{4-[2-(3,4,5-Trimethoxyphenoxy)ethyl]-1-piperazinylcarbonyl}-3,4-dihydrocarbostyril monohydrochloride ½ hydrate Colorless powdery crystals
Melting point: 238.5°-240° C.

6-[4-(2-Chloropropyl)-1-piperazinylcarbonyl]-3,4-dihydrocarbostyril monohydrochloride Colorless powdery crystals
Melting point: 238°-239° C. (decomposed)

6-(4-Ethoxycarbonylmethyl-1-piperazinylcarbonyl)-3,4-dihydrocarbostyril monohydrochloride Colorless powdery crystals
Melting point: 232°-234° C. (decomposed)

6-[4-(2-Ethoxycarbonylethyl)-1-piperazinylcarbonyl]-3,4-dihydrocarbostyril monohydrochloride Colorless powdery crystals Melting point: 227°–229.5° C. (decomposed)

6-(4-Propyl-1-piperazinylcarbonyl)-3,4-dihydrocarbostyril monohydrochloride ½-hydrate Colorless flake-like crystals
Melting point: 259°–262° C.

6-(4-Isopentyl-1-piperazinylcarbonyl)-3,4-dihydrocarbostyril monohydrochloride

Colorless flake-like crystals
Melting point: over 300° C.

8-(4-Benzyl-1-piperazinylcarbonyl)carbostyril monohydrochloride 3/2-hydrate

Colorless powdery crystals
Melting point: 177°–180° C.

5-(4-Benzyl-1-piperazinylcarbonyl)carbostyril monohydrochloride monohydrate

Colorless granular crystals
Melting point: 204°–207° C.

EXAMPLE 133

1.2 Grams of acetic anhydride and 0.6 g of formic acid were stirred at 60° C. for 2 hours, then 1.0 g of 6-(1-piperazinylcarbonyl)carbostyril was added thereto and the mixture was stirred at a room temperature for 1 hour. After the reaction was completed, the reaction mixture was poured into water and neutralized with 1N-sodium hydroxide aqueous solution, then extracted with chloroform. The organic layer was washed with water and a saturated sodium chloride aqueous solution in this order, the organic layer was dried with anhydrous sodium sulfate and the solvent was removed by distillation under a reduced pressure. The residue obtained was crystallized by adding ether and the crude crystals obtained were recrystallized from ethanol to obtain 0.15 g of 6-(4-formly-1-piperazinylcarbonyl)-3,4-dihydrocarbostyril. Colorless powdery crystals. Melting point: 198°–201° C.

EXAMPLE 134

0.5 Gram of 6-[4-(2-hydroxypropyl)-1-piperazinylcarbonyl]-3,4-dihydrocarbostyril and 0.3 ml of triethylamine were dissolved in 10 ml of dichloromethane, the mixture was stirred at a room temperature, 0.15 g of acetyl chloride was added slowly thereto and further stirred at a room temperature for 1 hour. The reaction mixture was poured into a saturated sodium bicarbonate aqueous solution and extracted with chloroform. The organic layer was washed with water and a saturated sodium chloride aqueous solution and extracted with chloroform. The organic layer was washed with water and a saturated sodium chloride aqueous solution then dried with anhydrous sodium sulfate. The solvent was removed by distillation under a reduced pressure and the residue obtained was treated by means of a silica gel column chromatography, then the objective product was dissolved in methanol and converted into the hydrochloride by adding a concentrated hydrochloric acid. Recrystallized from water-acetone to obtain 0.22 g of 6-[4-(2-acetoxypropyl)-1-piperazinylcarbonyl]-3,4-dihydrocarbostyril monohydrochloride. Melting point: 239°–241° C. (decomposed).

EXAMPLE 135

3.76 Grams of 6-(4-acetylmethyl-1-piperazinylcarbonyl)-3,4-dihydrocarbostyril monohydrochloride was dissolved in 50 ml of methanol, under ice-cooled condition, 0.44 g of sodium borohydride (NaBH4) was added slowly and then stirred at a room temperature for 1 hour. After the reaction was completed, a concentrated hydrochloric acid was added to ajust the pH of the reaction mixture to about pH 1, then most portion of the solvent was removed by distillation under a reduced pressure and the residue was extracted with 1N—NaOH-chloroform. The organic layer was washed with water and dried with anhydrous sodium sulfate, then the solvent was removed by distillation. The residue obtained was treated by means of a column chromatography and recrystallized from ethanol to obtain 2.26 g of 6-[4-(2-hydroxypropyl)-1-piperazinylcarbonyl]-3,4-dihydrocarbostyril. Colorless flake-like crystals. Melting point: 156°–157.5° C.

EXAMPLE 136

By a method similar to that described in Examples 6, 114, 119, 120, 122, 123, 124, 125, 126, 127, 128 and 129 and using a suitable starting material, there is obtained compound as follows:

6-[4-(4-Methoxyphenyl)acetyl-1-piperazinylcarbonyl]-3,4-dihydrocarbostyril

Colorless powdery crystals
Melting point: 158°–160° C.

EXAMPLE 137

By a method similar to that described in Examples 119, 120, 122–124 and 131, and using a follows:

5-(1-Piperazinylcarbonyl)carbostyril monohydrochloride ½-hydrate

Colorless granular crystals
Melting point: over 300° C.

7-(1-Piperazinylcarbonyl)-3,4-dihydrocarbostyril monohydrochloride

Colorless granular crystals
Melting point: 261.5°–263° C.

8-(1-Piperazinylcarbonyl)carbostyril

Colorless granular crystals
Melting point: over 300° C.

What is claimed is:

1. A carbostyril derivative or a pharmaceutically acceptable salt thereof said derivative being represented by the formula (1),

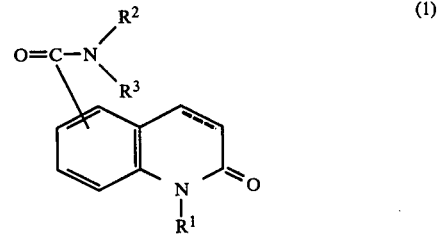

wherein $R^1$ is a hydrogen atom, a lower alkyl group, a lower alkenyl group, a lower alkynyl group or a phenyl-lower alkyl group; $R^2$ and $R^3$ may be the same or different and each is a lower alkyl group which may have one hydroxy group or one halogen atom as the substituent, or a phenyl-lower alkyl group which may have 1 to 3 substituents selected from the group consisting of a lower alkoxy group and a halogen atom on the phenyl ring, or said phenyl-lower alkyl group may have a lower alkylene-dioxy group as the substituent on the phenyl ring; further $R^2$ and $R^3$ may form, together with the adjacent nitrogen and without an additional heteroatom, a 5- or 6-membered saturated heterocyclic ring which may have a lower alkyl group or a phenyl-lower alkyl group as the substituent; the carbon-carbon bond between 3- and 4-positions in the carbostyril skeleton being a single or double bond.

2. A cardiotonic composition containing an effective amount of a carbostyril derivative of claim 1 or one of its pharmaceutically acceptable salts as the active ingredient.

* * * * *